(12) United States Patent
Garman

(10) Patent No.: US 11,266,714 B2
(45) Date of Patent: *Mar. 8, 2022

(54) CHLORIDE SALT OF TAT-NR2B9C

(71) Applicant: NoNO Inc., Toronto (CA)

(72) Inventor: Jonathan David Garman, Thornhill (CA)

(73) Assignee: NoNO Inc., Toronto (CA)

(*) Notice: Subject to any disclaimer, the term of this patent is extended or adjusted under 35 U.S.C. 154(b) by 0 days.

This patent is subject to a terminal disclaimer.

(21) Appl. No.: 16/904,230

(22) Filed: Jun. 17, 2020

(65) Prior Publication Data

US 2020/0384071 A1 Dec. 10, 2020

Related U.S. Application Data

(63) Continuation of application No. 16/128,423, filed on Sep. 11, 2018, now Pat. No. 10,758,589, which is a continuation of application No. 15/313,940, filed as application No. PCT/IB2015/053995 on May 28, 2015, now Pat. No. 10,206,973.

(60) Provisional application No. 62/004,142, filed on May 28, 2014.

(51) Int. Cl.

| | |
|---|---|
| *A61K 38/10* | (2006.01) |
| *A61K 47/64* | (2017.01) |
| *C07K 7/08* | (2006.01) |
| *C07K 19/00* | (2006.01) |
| *A61K 38/16* | (2006.01) |
| *A61K 9/19* | (2006.01) |
| *C07K 14/705* | (2006.01) |
| *C07K 7/06* | (2006.01) |
| *C07K 14/16* | (2006.01) |
| *A61K 9/00* | (2006.01) |
| *A61K 47/12* | (2006.01) |
| *A61K 47/18* | (2017.01) |
| *A61K 47/26* | (2006.01) |
| *C07K 14/005* | (2006.01) |
| *A61K 38/00* | (2006.01) |

(52) U.S. Cl.
CPC .......... *A61K 38/162* (2013.01); *A61K 9/0019* (2013.01); *A61K 9/19* (2013.01); *A61K 38/10* (2013.01); *A61K 47/12* (2013.01); *A61K 47/183* (2013.01); *A61K 47/26* (2013.01); *A61K 47/645* (2017.08); *C07K 7/06* (2013.01); *C07K 7/08* (2013.01); *C07K 14/005* (2013.01); *C07K 14/16* (2013.01); *C07K 14/163* (2013.01); *C07K 14/705* (2013.01); *C07K 19/00* (2013.01); *A61K 38/00* (2013.01); *C07K 2319/10* (2013.01); *C12N 2740/16322* (2013.01)

(58) Field of Classification Search
CPC ...... A61K 38/08; A61K 38/10; A61K 47/645; C07K 7/06; C07K 7/08; C07K 2319/10
See application file for complete search history.

(56) References Cited

U.S. PATENT DOCUMENTS

| | | | |
|---|---|---|---|
| 7,060,268 | B2 | 6/2006 | Andya et al. |
| 7,879,805 | B2 | 2/2011 | Chen et al. |
| 10,206,878 | B2 | 2/2019 | Garman et al. |
| 10,206,973 | B2 | 2/2019 | Garman |
| 10,251,935 | B2 | 4/2019 | Garman |
| 10,758,589 | B2 | 9/2020 | Garman |
| 2001/0014326 | A1 | 8/2001 | Andya et al. |
| 2013/0156704 | A1 | 6/2013 | Tymianski |
| 2014/0162957 | A1 | 6/2014 | Garman |
| 2017/0035838 | A1 | 2/2017 | Garman |
| 2017/0112769 | A1 | 4/2017 | Garman et al. |
| 2019/0175689 | A1 | 6/2019 | Garman |

FOREIGN PATENT DOCUMENTS

| | | |
|---|---|---|
| WO | WO 07/016366 A2 | 2/2007 |
| WO | WO 07/124090 A2 | 11/2007 |
| WO | WO 10/144721 A2 | 12/2010 |
| WO | WO 12/021854 A2 | 2/2012 |
| WO | WO 12/156308 A1 | 11/2012 |
| WO | WO 12/176172 A2 | 12/2012 |
| WO | WO 14/076655 A1 | 5/2014 |
| WO | WO 14/085349 A1 | 6/2014 |
| WO | WO 15/181756 A1 | 12/2015 |
| WO | WO 15/181757 A1 | 12/2015 |

OTHER PUBLICATIONS

Daugherty et al., "Formulation and delivery issues for monoclonal antibody therapeutics," Advanced Drug Delivery Reviews, 58:686-706, (2006).

Patro et al., "Protein formulation and fill-finish operations," Biotechnology Annual Review, 8:55-84, (2002).

Roux et al., "Elimination and exchange of trifluoroacetate counter-ion from cationic peptides: a critical evaluation of different approaches," J. Pept. Sci., 14:354-359, doi: 10.1002/psc.951, (2008). [Published online Nov. 26, 2007].

(Continued)

*Primary Examiner* — Jeffrey E. Russel
(74) *Attorney, Agent, or Firm* — Alston & Bird LLP

(57) ABSTRACT

The present invention provides lyophilized formulations of active agents, particularly of TAT-NR2B9c, as chloride salts. TAT-NR2B9c has shown promise for treating stroke, aneurysm, subarachnoid hemorrhage and other neurological or neurotraumatic conditions. The chloride salt of TAT-NR2B9c shows improved stability compared with the acetate salt form of prior formulations. Formulations of the chloride salt of TAT-NR2B9c are stable at ambient temperature thus facilitating maintenance of supplies of such a formulation in ambulances for administration at the scene of illness or accident or in transit to a hospital.

30 Claims, 10 Drawing Sheets

Figure 1:
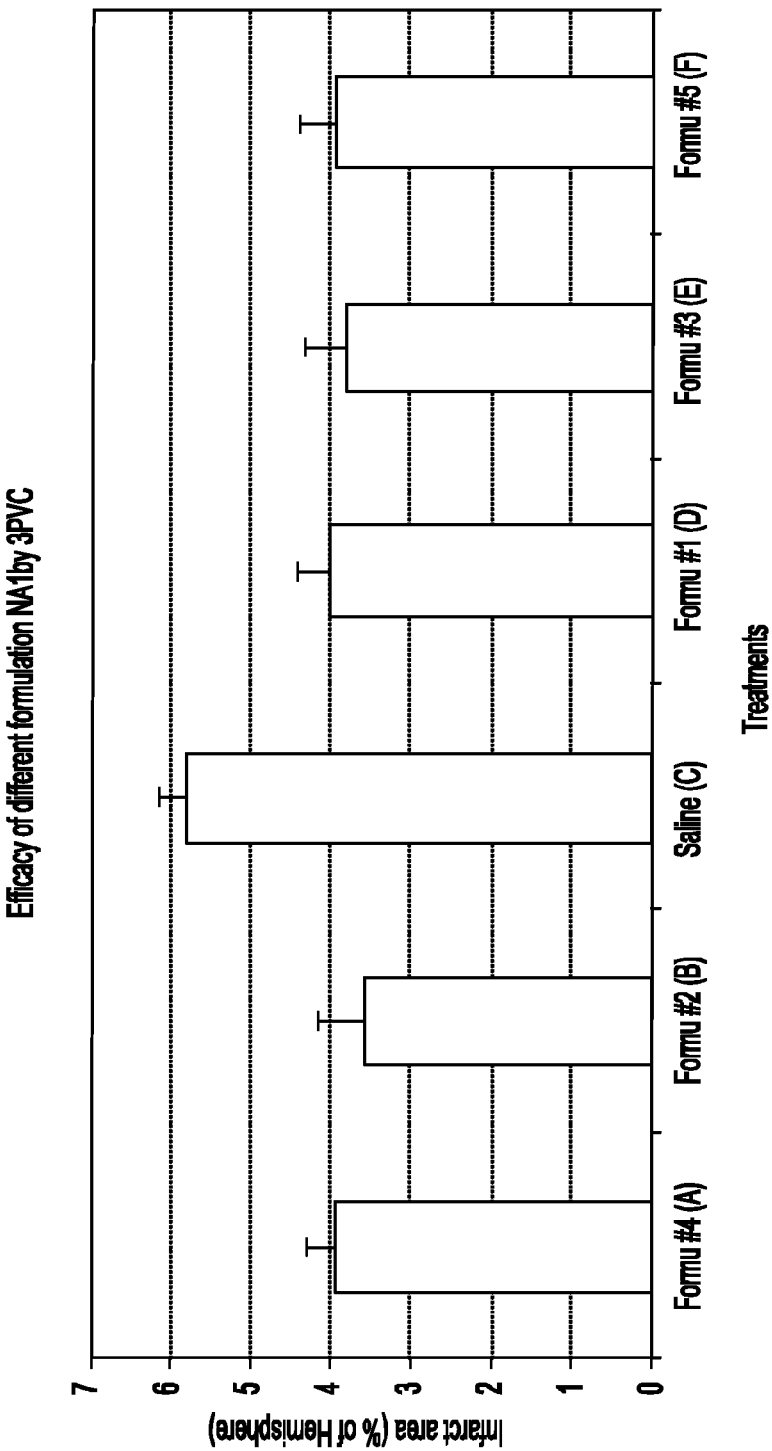

Specification includes a Sequence Listing.

(56) References Cited

OTHER PUBLICATIONS

Wang "Instability, stabilization, and formulation of liquid protein pharmaceuticals," International Journal of Pharmaceutics, 185:129-188, (1999).
Wang et al., "Lyophilization and development of solid protein pharmaceuticals," International Journal of Pharmaceutics, 203:1-60, (2000). [Received Sep. 9, 1999].
EPO Application No. 15799583.8 (Published as EP3149048), Supplementary European Search Report and European Search Opinion dated Dec. 5, 2017.
U.S. Appl. No. 15/313,940, Non-Final Office Action dated Jan. 5, 2018.
U.S. Appl. No. 15/313,940, Notice of Allowance dated Aug. 31, 2018.
U.S. Appl. No. 16/128,423, Final Office Action dated Nov. 26, 2019.
U.S. Appl. No. 16/128,423, Non-Final Office Action dated Aug. 6, 2019.
U.S. Appl. No. 16/128,423, Notice of Allowance dated Mar. 4, 2020.
U.S. Appl. No. 16/128,423, Notice of Allowance dated Apr. 22, 2020.
WIPO Application No. PCT/IB2015/053995, PCT International Preliminary Report on Patentability dated Dec. 8, 2016.
WIPO Application No. PCT/IB2015/053995, PCT International Search Report and Written Opinion of the International Searching Authority dated Sep. 1, 2015.
EPO Application No. 20152821.3 Supplementary European Search Report and European Search Opinion dated Nov. 5, 2020.

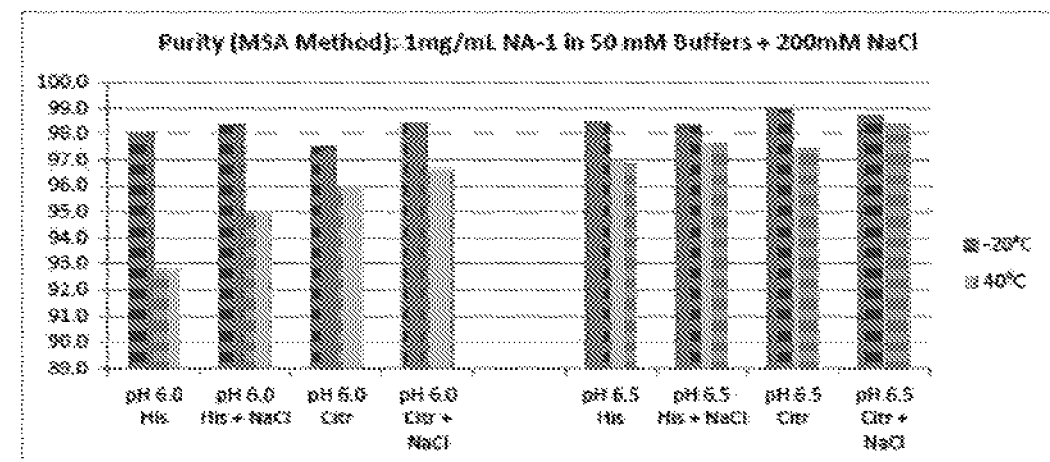
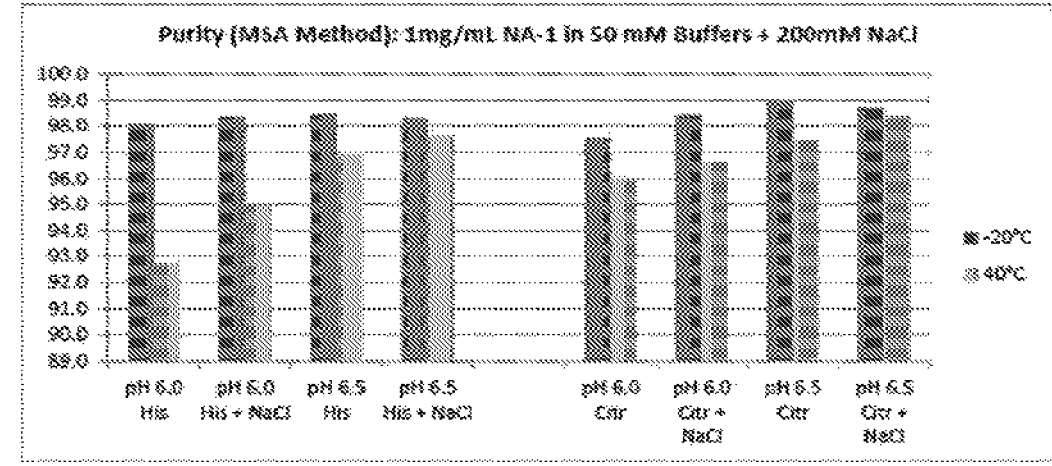
FIG. 2A, B

 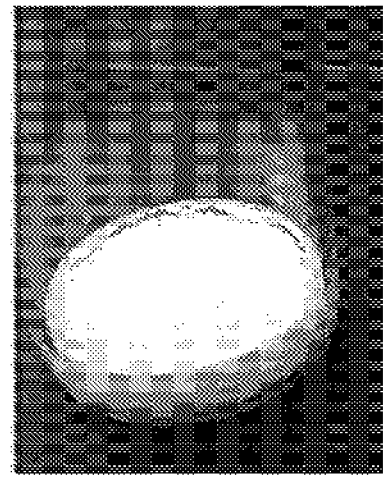
Small scale 4 NA-1
Formulations 1-3 from small scale 6
FIG. 7A, B

SEQUENCE LISTING

<160> NUMBER OF SEQ ID NOS: 73

<210> SEQ ID NO 1
<211> LENGTH: 10
<212> TYPE: PRT
<213> ORGANISM: Artificial Sequence
<220> FEATURE:
<223> OTHER INFORMATION: Synthesized

<400> SEQUENCE: 1

Gly Arg Lys Lys Arg Arg Gln Arg Arg Arg
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthesized

<400> SEQUENCE: 2

Tyr Gly Arg Lys Lys Arg Arg Gln Arg Arg Arg
1               5                   10

```
<210> SEQ ID NO 3
<211> LENGTH: 11
<212> TYPE: PRT
<213> ORGANISM: Artificial Sequence
<220> FEATURE:
<223> OTHER INFORMATION: Synthesized

<400> SEQUENCE: 3

Phe Gly Arg Lys Lys Arg Arg Gln Arg Arg Arg
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthesized

<400> SEQUENCE: 4

Gly Arg Lys Lys Arg Arg Gln Arg Arg Arg Pro Gln
1               5                   10

<210> SEQ ID NO 5
<211> LENGTH: 9
<212> TYPE: PRT
<213> ORGANISM: Artificial Sequence
<220> FEATURE:
<223> OTHER INFORMATION: Synthesized

<400> SEQUENCE: 5

Lys Leu Ser Ser Ile Glu Ser Asp Val
1               5

<210> SEQ ID NO 6
<211> LENGTH: 20
<212> TYPE: PRT
<213> ORGANISM: Artificial Sequence
<220> FEATURE:
<223> OTHER INFORMATION: Synthesized

<400> SEQUENCE: 6

Tyr Gly Arg Lys Lys Arg Arg Gln Arg Arg Arg Lys Leu Ser Ser Ile
1               5                   10                  15

Glu Ser Asp Val
            20

<210> SEQ ID NO 7
<211> LENGTH: 20
<212> TYPE: PRT
<213> ORGANISM: Artificial Sequence
<220> FEATURE:
<223> OTHER INFORMATION: Synthesized

<400> SEQUENCE: 7

Tyr Gly Arg Lys Lys Arg Arg Gln Arg Arg Arg Lys Leu Ser Ser Ile
1               5                   10                  15

Glu Thr Asp Val
            20

<210> SEQ ID NO 8
<211> LENGTH: 12
<212> TYPE: PRT
<213> ORGANISM: Artificial Sequence
<220> FEATURE:
<223> OTHER INFORMATION: Synthesized
<220> FEATURE:
<221> NAME/KEY: VARIANT
```

```
<222> LOCATION: 1
<223> OTHER INFORMATION: Xaa = Blank or any amino acid

<400> SEQUENCE: 8

Xaa Phe Gly Arg Lys Lys Arg Arg Gln Arg Arg Arg
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Synthesized

<400> SEQUENCE: 9

Arg Leu Ser Gly Met Asn Glu Val Leu Ser Phe Arg Trp Leu
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Synthesized

<400> SEQUENCE: 10

Arg Arg Arg Gln Arg Arg Lys Lys Arg
1               5

<210> SEQ ID NO 11
<211> LENGTH: 20
<212> TYPE: PRT
<213> ORGANISM: Artificial Sequence
<220> FEATURE:
<223> OTHER INFORMATION: Synthesized

<400> SEQUENCE: 11

Phe Asn Gly Ser Ser Asn Gly His Val Tyr Glu Lys Leu Ser Ser Ile
1               5                   10                  15

Glu Ser Asp Val
            20

<210> SEQ ID NO 12
<211> LENGTH: 4
<212> TYPE: PRT
<213> ORGANISM: Artificial Sequence
<220> FEATURE:
<223> OTHER INFORMATION: Synthesized

<400> SEQUENCE: 12

Glu Ser Asp Val
1

<210> SEQ ID NO 13
<211> LENGTH: 20
<212> TYPE: PRT
<213> ORGANISM: Artificial Sequence
<220> FEATURE:
<223> OTHER INFORMATION: Synthesized

<400> SEQUENCE: 13

His Pro Thr Asp Ile Thr Gly Pro Leu Asn Leu Ser Asp Pro Ser Val
1               5                   10                  15

Ser Thr Val Val
            20
```

<210> SEQ ID NO 14
<211> LENGTH: 20
<212> TYPE: PRT
<213> ORGANISM: Artificial Sequence
<220> FEATURE:
<223> OTHER INFORMATION: Synthesized

<400> SEQUENCE: 14

Arg Arg Ala Ile Glu Arg Glu Glu Gly Gln Leu Gln Leu Cys Ser Arg
1               5                   10                  15

His Arg Glu Ser
            20

<210> SEQ ID NO 15
<211> LENGTH: 20
<212> TYPE: PRT
<213> ORGANISM: Artificial Sequence
<220> FEATURE:
<223> OTHER INFORMATION: Synthesized

<400> SEQUENCE: 15

Thr Gln Gly Phe Pro Gly Pro Cys Thr Trp Arg Arg Ile Ser Ser Leu
1               5                   10                  15

Glu Ser Glu Val
            20

<210> SEQ ID NO 16
<211> LENGTH: 20
<212> TYPE: PRT
<213> ORGANISM: Artificial Sequence
<220> FEATURE:
<223> OTHER INFORMATION: Synthesized

<400> SEQUENCE: 16

Ala Val Ser Arg Lys Thr Glu Leu Glu Glu Tyr Gln Arg Thr Ser Arg
1               5                   10                  15

Thr Cys Glu Ser
            20

<210> SEQ ID NO 17
<211> LENGTH: 20
<212> TYPE: PRT
<213> ORGANISM: Artificial Sequence
<220> FEATURE:
<223> OTHER INFORMATION: Synthesized

<400> SEQUENCE: 17

Leu Asn Ser Cys Ser Asn Arg Arg Val Tyr Lys Lys Met Pro Ser Ile
1               5                   10                  15

Glu Ser Asp Val
            20

<210> SEQ ID NO 18
<211> LENGTH: 20
<212> TYPE: PRT
<213> ORGANISM: Artificial Sequence
<220> FEATURE:
<223> OTHER INFORMATION: Synthesized

<400> SEQUENCE: 18

Gly Gly Asp Leu Gly Thr Arg Arg Gly Ser Ala His Phe Ser Ser Leu
1               5                   10                  15

Glu Ser Glu Val
            20

<210> SEQ ID NO 19
<211> LENGTH: 20
<212> TYPE: PRT
<213> ORGANISM: Artificial Sequence
<220> FEATURE:
<223> OTHER INFORMATION: Synthesized

<400> SEQUENCE: 19

Gln Pro Thr Pro Thr Leu Gly Leu Asn Leu Gly Asn Asp Pro Asp Arg
1               5                   10                  15

Gly Thr Ser Ile
            20

<210> SEQ ID NO 20
<211> LENGTH: 20
<212> TYPE: PRT
<213> ORGANISM: Artificial Sequence
<220> FEATURE:
<223> OTHER INFORMATION: Synthesized

<400> SEQUENCE: 20

Met Gln Ser Ile Pro Cys Met Ser His Ser Ser Gly Met Pro Leu Gly
1               5                   10                  15

Ala Thr Gly Leu
            20

<210> SEQ ID NO 21
<211> LENGTH: 20
<212> TYPE: PRT
<213> ORGANISM: Artificial Sequence
<220> FEATURE:
<223> OTHER INFORMATION: Synthesized

<400> SEQUENCE: 21

Gln Asn Phe Ala Thr Tyr Lys Glu Gly Tyr Asn Val Tyr Gly Ile Glu
1               5                   10                  15

Ser Val Lys Ile
            20

<210> SEQ ID NO 22
<211> LENGTH: 20
<212> TYPE: PRT
<213> ORGANISM: Artificial Sequence
<220> FEATURE:
<223> OTHER INFORMATION: Synthesized

<400> SEQUENCE: 22

Gln Asn Tyr Ala Thr Tyr Arg Glu Gly Tyr Asn Val Tyr Gly Thr Glu
1               5                   10                  15

Ser Val Lys Ile
            20

<210> SEQ ID NO 23
<211> LENGTH: 20
<212> TYPE: PRT
<213> ORGANISM: Artificial Sequence
<220> FEATURE:
<223> OTHER INFORMATION: Synthesized

<400> SEQUENCE: 23

His Thr Gly Thr Ala Ile Arg Gln Ser Ser Gly Leu Ala Val Ile Ala
1               5                   10                  15

Ser Asp Leu Pro

20

<210> SEQ ID NO 24
<211> LENGTH: 20
<212> TYPE: PRT
<213> ORGANISM: Artificial Sequence
<220> FEATURE:
<223> OTHER INFORMATION: Synthesized

<400> SEQUENCE: 24

Ser Phe Thr Ser Ile Leu Thr Cys His Gln Arg Arg Thr Gln Arg Lys
1               5                   10                  15

Glu Thr Val Ala
            20

<210> SEQ ID NO 25
<211> LENGTH: 20
<212> TYPE: PRT
<213> ORGANISM: Artificial Sequence
<220> FEATURE:
<223> OTHER INFORMATION: Synthesized

<400> SEQUENCE: 25

Glu Val Ile Asn Met His Thr Phe Asn Asp Arg Arg Leu Pro Gly Lys
1               5                   10                  15

Glu Thr Met Ala
            20

<210> SEQ ID NO 26
<211> LENGTH: 5
<212> TYPE: PRT
<213> ORGANISM: Artificial Sequence
<220> FEATURE:
<223> OTHER INFORMATION: Synthesized

<400> SEQUENCE: 26

Ile Glu Thr Ala Val
1               5

<210> SEQ ID NO 27
<211> LENGTH: 4
<212> TYPE: PRT
<213> ORGANISM: Artificial Sequence
<220> FEATURE:
<223> OTHER INFORMATION: Synthesized

<400> SEQUENCE: 27

Ser Thr Val Val
1

<210> SEQ ID NO 28
<211> LENGTH: 4
<212> TYPE: PRT
<213> ORGANISM: Artificial Sequence
<220> FEATURE:
<223> OTHER INFORMATION: Synthesized

<400> SEQUENCE: 28

His Arg Glu Ser
1

<210> SEQ ID NO 29
<211> LENGTH: 4
<212> TYPE: PRT
<213> ORGANISM: Artificial Sequence
<220> FEATURE:

```
<223> OTHER INFORMATION: Synthesized

<400> SEQUENCE: 29

Glu Ser Glu Val
1

<210> SEQ ID NO 30
<211> LENGTH: 4
<212> TYPE: PRT
<213> ORGANISM: Artificial Sequence
<220> FEATURE:
<223> OTHER INFORMATION: Synthesized

<400> SEQUENCE: 30

Thr Cys Glu Ser
1

<210> SEQ ID NO 31
<211> LENGTH: 4
<212> TYPE: PRT
<213> ORGANISM: Artificial Sequence
<220> FEATURE:
<223> OTHER INFORMATION: Synthesized

<400> SEQUENCE: 31

Gly Thr Ser Ile
1

<210> SEQ ID NO 32
<211> LENGTH: 4
<212> TYPE: PRT
<213> ORGANISM: Artificial Sequence
<220> FEATURE:
<223> OTHER INFORMATION: Synthesized

<400> SEQUENCE: 32

Ala Thr Gly Leu
1

<210> SEQ ID NO 33
<211> LENGTH: 4
<212> TYPE: PRT
<213> ORGANISM: Artificial Sequence
<220> FEATURE:
<223> OTHER INFORMATION: Synthesized

<400> SEQUENCE: 33

Ser Val Lys Ile
1

<210> SEQ ID NO 34
<211> LENGTH: 4
<212> TYPE: PRT
<213> ORGANISM: Artificial Sequence
<220> FEATURE:
<223> OTHER INFORMATION: Synthesized

<400> SEQUENCE: 34

Ser Asp Leu Pro
1

<210> SEQ ID NO 35
<211> LENGTH: 4
<212> TYPE: PRT
<213> ORGANISM: Artificial Sequence
<220> FEATURE:
<223> OTHER INFORMATION: Synthesized
```

```
<400> SEQUENCE: 35

Glu Thr Val Ala
1

<210> SEQ ID NO 36
<211> LENGTH: 4
<212> TYPE: PRT
<213> ORGANISM: Artificial Sequence
<220> FEATURE:
<223> OTHER INFORMATION: Synthesized

<400> SEQUENCE: 36

Glu Thr Met Ala
1

<210> SEQ ID NO 37
<211> LENGTH: 20
<212> TYPE: PRT
<213> ORGANISM: Artificial Sequence
<220> FEATURE:
<223> OTHER INFORMATION: Synthesized

<400> SEQUENCE: 37

Arg Arg Arg Gln Arg Arg Lys Lys Arg Gly Tyr Lys Leu Ser Ser Ile
1               5                   10                  15

Glu Thr Asp Val
            20

<210> SEQ ID NO 38
<211> LENGTH: 4
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = E, D, N, or Q
<220> FEATURE:
<221> NAME/KEY: VARIANT
<222> LOCATION: 2
<223> OTHER INFORMATION: Xaa = S or T
<220> FEATURE:
<221> NAME/KEY: VARIANT
<222> LOCATION: 3
<223> OTHER INFORMATION: Xaa = D, E, Q, or N
<220> FEATURE:
<221> NAME/KEY: VARIANT
<222> LOCATION: 4
<223> OTHER INFORMATION: Xaa = V or L

<400> SEQUENCE: 38

Xaa Xaa Xaa Xaa
1

<210> SEQ ID NO 39
<211> LENGTH: 4
<212> TYPE: PRT
<213> ORGANISM: Artificial Sequence
<220> FEATURE:
<223> OTHER INFORMATION: Synthesized

<400> SEQUENCE: 39

Glu Thr Asp Val
1

<210> SEQ ID NO 40
```

```
<211> LENGTH: 4
<212> TYPE: PRT
<213> ORGANISM: Artificial Sequence
<220> FEATURE:
<223> OTHER INFORMATION: Synthesized

<400> SEQUENCE: 40

Glu Thr Glu Val
1

<210> SEQ ID NO 41
<211> LENGTH: 4
<212> TYPE: PRT
<213> ORGANISM: Artificial Sequence
<220> FEATURE:
<223> OTHER INFORMATION: Synthesized

<400> SEQUENCE: 41

Asp Thr Asp Val
1

<210> SEQ ID NO 42
<211> LENGTH: 4
<212> TYPE: PRT
<213> ORGANISM: Artificial Sequence
<220> FEATURE:
<223> OTHER INFORMATION: Synthesized

<400> SEQUENCE: 42

Asp Thr Glu Val
1

<210> SEQ ID NO 43
<211> LENGTH: 9
<212> TYPE: PRT
<213> ORGANISM: Artificial Sequence
<220> FEATURE:
<223> OTHER INFORMATION: Synthesized

<400> SEQUENCE: 43

Lys Leu Ser Ser Ile Glu Thr Asp Val
1               5

<210> SEQ ID NO 44
<211> LENGTH: 5
<212> TYPE: PRT
<213> ORGANISM: Artificial Sequence
<220> FEATURE:
<223> OTHER INFORMATION: Synthesized

<400> SEQUENCE: 44

Gly Ser Ser Ser Ser
1               5

<210> SEQ ID NO 45
<211> LENGTH: 5
<212> TYPE: PRT
<213> ORGANISM: Artificial Sequence
<220> FEATURE:
<223> OTHER INFORMATION: Synthesized

<400> SEQUENCE: 45

Thr Gly Glu Lys Pro
1               5

<210> SEQ ID NO 46
<211> LENGTH: 8
```

```
<212> TYPE: PRT
<213> ORGANISM: Artificial Sequence
<220> FEATURE:
<223> OTHER INFORMATION: Synthesized

<400> SEQUENCE: 46

Gly Gly Arg Arg Gly Gly Gly Ser
1               5

<210> SEQ ID NO 47
<211> LENGTH: 9
<212> TYPE: PRT
<213> ORGANISM: Artificial Sequence
<220> FEATURE:
<223> OTHER INFORMATION: Synthesized

<400> SEQUENCE: 47

Leu Arg Gln Arg Asp Gly Glu Arg Pro
1               5

<210> SEQ ID NO 48
<211> LENGTH: 13
<212> TYPE: PRT
<213> ORGANISM: Artificial Sequence
<220> FEATURE:
<223> OTHER INFORMATION: Synthesized

<400> SEQUENCE: 48

Tyr Gly Arg Lys Lys Arg Arg Gln Arg Arg Arg Pro Gln
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = Blank or an amino acid that is not Y

<400> SEQUENCE: 49

Xaa Gly Arg Lys Lys Arg Arg Gln Arg Arg Arg
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = Blank or any amino acid

<400> SEQUENCE: 50

Xaa Gly Lys Lys Lys Lys Gln Lys Lys Lys
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Synthesized
<220> FEATURE:
<221> NAME/KEY: VARIANT
```

```
<222> LOCATION: 1
<223> OTHER INFORMATION: Xaa = Blank or any amino acid

<400> SEQUENCE: 51

Xaa Arg Lys Lys Arg Arg Gln Arg Arg Arg
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = Blank or any amino acid

<400> SEQUENCE: 52

Xaa Gly Ala Lys Lys Arg Arg Gln Arg Arg Arg
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = Blank or any amino acid

<400> SEQUENCE: 53

Xaa Ala Lys Lys Arg Arg Gln Arg Arg Arg
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = Blank or any amino acid

<400> SEQUENCE: 54

Xaa Gly Arg Lys Ala Arg Arg Gln Arg Arg Arg
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = Blank or any amino acid

<400> SEQUENCE: 55

Xaa Arg Lys Ala Arg Arg Gln Arg Arg Arg
1               5                   10

<210> SEQ ID NO 56
<211> LENGTH: 11
```

```
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = Blank or any amino acid

<400> SEQUENCE: 56

Xaa Gly Arg Lys Lys Ala Arg Gln Arg Arg
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = Blank or any amino acid

<400> SEQUENCE: 57

Xaa Arg Lys Lys Ala Arg Gln Arg Arg Arg
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = Blank or any amino acid

<400> SEQUENCE: 58

Xaa Gly Arg Lys Lys Arg Arg Gln Ala Arg Arg
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = Blank or any amino acid

<400> SEQUENCE: 59

Xaa Arg Lys Lys Arg Arg Gln Ala Arg Arg
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = Blank or any amino acid

<400> SEQUENCE: 60
```

```
Xaa Gly Arg Lys Lys Arg Arg Gln Arg Ala Arg
1               5                   10
```

<210> SEQ ID NO 61
<211> LENGTH: 10
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = Blank or any amino acid

<400> SEQUENCE: 61

```
Xaa Arg Lys Lys Arg Arg Gln Arg Ala Arg
1               5                   10
```

<210> SEQ ID NO 62
<211> LENGTH: 12
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = Blank or any amino acid

<400> SEQUENCE: 62

```
Xaa Arg Arg Pro Arg Arg Pro Arg Arg Pro Arg Arg
1               5                   10
```

<210> SEQ ID NO 63
<211> LENGTH: 12
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = Blank or any amino acid

<400> SEQUENCE: 63

```
Xaa Arg Arg Ala Arg Arg Ala Arg Arg Ala Arg Arg
1               5                   10
```

<210> SEQ ID NO 64
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = Blank or any amino acid

<400> SEQUENCE: 64

```
Xaa Arg Arg Arg Ala Arg Arg Arg Ala Arg Arg
1               5                   10
```

<210> SEQ ID NO 65
<211> LENGTH: 11
<212> TYPE: PRT
<213> ORGANISM: Artificial Sequence
<220> FEATURE:
<223> OTHER INFORMATION: Synthesized
<220> FEATURE:

```
<221> NAME/KEY: VARIANT
<222> LOCATION: 1
<223> OTHER INFORMATION: Xaa = Blank or any amino acid

<400> SEQUENCE: 65

Xaa Arg Arg Arg Pro Arg Arg Pro Arg Arg
1               5                   10

<210> SEQ ID NO 66
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = Blank or any amino acid

<400> SEQUENCE: 66

Xaa Arg Arg Pro Arg Arg Pro Arg Arg
1               5

<210> SEQ ID NO 67
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = Blank or any amino acid

<400> SEQUENCE: 67

Xaa Arg Arg Ala Arg Arg Ala Arg Arg
1               5

<210> SEQ ID NO 68
<211> LENGTH: 4
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = E, Q, A, or an analog therof
<220> FEATURE:
<221> NAME/KEY: VARIANT
<222> LOCATION: 2
<223> OTHER INFORMATION: Xaa = T or S
<220> FEATURE:
<221> NAME/KEY: VARIANT
<222> LOCATION: 3
<223> OTHER INFORMATION: Xaa = A, Q, D, N, N-Me-A, N-Me-Q, N-Me-D,
      N-Me-N, or an analogue thereof

<400> SEQUENCE: 68

Xaa Xaa Xaa Val
1

<210> SEQ ID NO 69
<211> LENGTH: 22
<212> TYPE: PRT
<213> ORGANISM: Artificial Sequence
<220> FEATURE:
<223> OTHER INFORMATION: Synthesized

<400> SEQUENCE: 69
```

```
Val Asp Ser Glu Ile Ser Ser Leu Lys Arg Arg Gln Arg Arg Lys
1               5                   10                  15

Lys Arg Gly Tyr Ile Asn
            20

<210> SEQ ID NO 70
<211> LENGTH: 20
<212> TYPE: PRT
<213> ORGANISM: Artificial Sequence
<220> FEATURE:
<223> OTHER INFORMATION: Synthesized

<400> SEQUENCE: 70

Arg Arg Arg Gln Arg Arg Lys Lys Arg Gly Tyr Lys Leu Ser Ser Ile
1               5                   10                  15

Glu Ser Asp Val
            20

<210> SEQ ID NO 71
<211> LENGTH: 5
<212> TYPE: PRT
<213> ORGANISM: Artificial Sequence
<220> FEATURE:
<223> OTHER INFORMATION: Synthesized

<400> SEQUENCE: 71

Ile Glu Ser Asp Val
1               5

<210> SEQ ID NO 72
<211> LENGTH: 11
<212> TYPE: PRT
<213> ORGANISM: Artificial Sequence
<220> FEATURE:
<223> OTHER INFORMATION: Synthesized

<400> SEQUENCE: 72

Gly Arg Lys Lys Arg Arg Gln Arg Arg Arg Pro
1               5                   10

<210> SEQ ID NO 73
<211> LENGTH: 5
<212> TYPE: PRT
<213> ORGANISM: Artificial Sequence
<220> FEATURE:
<223> OTHER INFORMATION: Synthesized

<400> SEQUENCE: 73

Ile Glu Thr Asp Val
1               5
```

CHLORIDE SALT OF TAT-NR2B9C

CROSS-REFERENCE TO RELATED APPLICATION

This application is a continuation of U.S. application Ser. No. 16/128,423 filed Sep. 11, 2018, which is a continuation of U.S. application Ser. No. 15/313,940 filed Nov. 23, 2016, which is a U.S. National Stage of PCT/IB2015/053995 filed May 28, 2015, which claims priority to U.S. Provisional Application No. 62/004,142 filed May 28, 2014, each of which is hereby incorporated by reference in its entirety for all purposes.

REFERENCE TO SEQUENCE LISTING

This application includes an electronic sequence listing in a file named 520184CON_SEQLST.TXT, created on Jun. 17, 2020 and containing 16,781 bytes, which is hereby incorporated by reference.

BACKGROUND

Tat-NR2B9c (also known as NA-1) is an agent that inhibits PSD-95, thus disrupting binding to N-methyl-D-aspartate receptors (NMDARs) and neuronal nitric oxide synthases (nNOS) and reducing excitoxicity induced by cerebral ischemia. Treatment reduces infarction size and functional deficits. TAT-NR2B9c has undergone a successful phase II trial (see WO 2010144721 and Aarts et al., Science 298, 846-850 (2002), Hill et al., Lancet Neurol. 11:942-950 (2012)).

Because TAT-NR2B9c is free of serious side effects, it can be administered when stroke or other ischemic conditions or hemorrhagic conditions is suspected without a diagnosis according to art-recognized criteria having been made to confirm that no hemorrhage is present. For example, TAT-NR2B9c can be administered at the location where the stroke or neurotrauma has occurred (e.g., in the patients' home) or in an ambulance transporting a subject to a hospital.

TAT-NR2B9c has previously been described as a liquid composition of normal saline or phosphate buffered saline or a lyophilized composition from normal saline (WO2010144721).

SUMMARY OF THE CLAIMED INVENTION

The invention provides a chloride salt of a peptide which is TAT-NR2B9c (SEQ ID NO:6) or differs from TAT-NR2B9c by up to 5 amino acid substitutions, insertions or deletions, or any other peptide disclosed as an active agent herein. The chloride salt can be prepared by exchanging trifluoroacetate for chloride in a trifluoroacetate salt of TAT-NR2B9c. The chloride salt can also be prepared by exchanging trifluoroacetate for acetate and then acetate for chloride staring from a trifluoroacetate salt of TAT-NR2B9c. Optionally, greater than 99% of anions in the salt are chloride.

The invention further provides a prelyophilized formulation comprising a chloride salt as described above a buffer and a sugar. Optionally, the chloride salt is a chloride salt of TAT-NR2B9c. Optionally, the buffer is histidine and the sugar is trehalose and the pH is 6-7. Optionally, acetate and trifluoroacetate each comprise less than 1% of anions by weight in the formulation. Optionally, acetate and trifluoroacetate each comprise less than 0.1% by weight of anions in the formulation. Optionally, the chloride salt of the peptide is at a concentration of 70-120 mg/ml, the histidine is at a concentration of 15-100 mM, and the trehalose is at a concentration of 80-160 mM. Optionally, the chloride salt of the peptide is at a concentration of 70-120 mg/ml, the histidine is at a concentration of 20-100 mM, and the trehalose is at a concentration of 100-140 mM. Optionally, the Tat-NR2B9c is at a concentration of 70-120 mg/ml, the concentration of histidine 20-50 mM, and the concentration of trehalose is 100-140 mM. Optionally, the concentration of histidine is 20 mM and the concentration of trehalose is 100-200 mM, preferably 120 mM and the concentration of TAT-NR2B9c is 90 mg/ml.

The invention further provides a lyophilized formulation prepared by lyophilizing any of the prelyophilized formulations described above. Optionally, acetate and trifluoroacetate each comprise less than 1% by weight of anions in the formulation. Optionally, acetate and trifluoroacetate each comprise less than 0.1% by weight of anions in the formulation.

The invention further provides a reconstituted formulation prepared by combining any of the lyophilized formulations described above with an aqueous solution. Optionally, the aqueous solution is water or normal saline. Optionally, the volume of the reconstituted formulation is 3-6 times the volume of the prelyophilized formulation.

The invention further provides a reconstituted formulation comprising TAT-NR2B9c or other active agent described herein at concentration of 15-25 mg/ml, a buffer and a sugar. Optionally, the buffer is histidine at a concentration of 4-20 mM and the sugar is trehalose at a concentration of 20-30 mM and the pH is 6-7. Optionally, the reconstituted formulation of claim 19 wherein acetate and trifluoroacetate each comprise less than 1% by weight of anions in the formulation. Optionally, acetate and trifluoroacetate each comprise less than 0.1% by weight of anions in the formulation.

The invention further provides a method of preparing a formulation, comprising storing a lyophilized formulation sample as described above for at least a week at a temperature of at least 20° C.; and reconstituting the lyophilized formulation. Optionally the lyophilized formulation is reconstituted in water or saline. Optionally, the method also includes administering the reconstituted formulation, optionally after further dilution in normal saline, to a patient. Optionally, the formulation is stored for at least a year. Optionally, the storage is at ambient temperature. Optionally, the storage includes periods in which the temperature exceeds 37° C. In some methods, the patient has stroke or traumatic injury to the CNS. In some methods, the lyophilized sample is stored in an ambulance. In some methods, the patient has a subarachnoid hemorrhage. In some methods, the patient is undergoing endovascular repair for an aneurysm.

BRIEF DESCRIPTIONS OF THE FIGURES

FIG. 1: Graph shows the infarct area of the rat brain after 3PVO stroke following treatment with different formulations of TAT-NR2B9c.

FIGS. 2A, B: A) Bar graph demonstrating the stability of different TAT-NR2B9c formulations at −20° C. and 40° C. Y axis represents purity of the TAT-NR2B9c after 1 week at the storage temperature as measured by % total area using RP-HPLC. B) same data as A, but sorted by buffer and pH.

Figure 3:
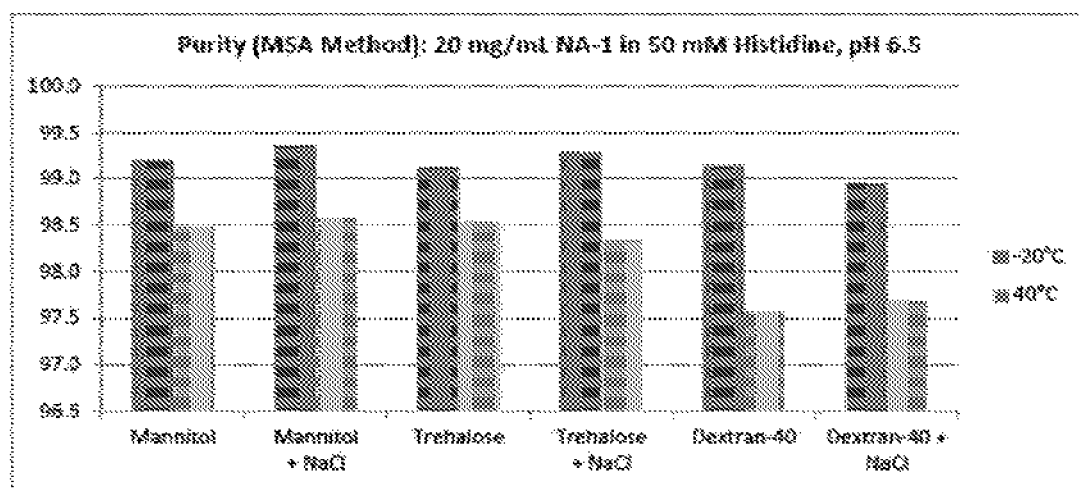

FIG. 3: Bar graph demonstrating the stability (by HPLC) of 20 mg/ml TAT-NR2B9c in Histidine buffer, pH 6.5, in the presence of different bulking agents and salt at −20° C. and 40° C.

Figure 4A:
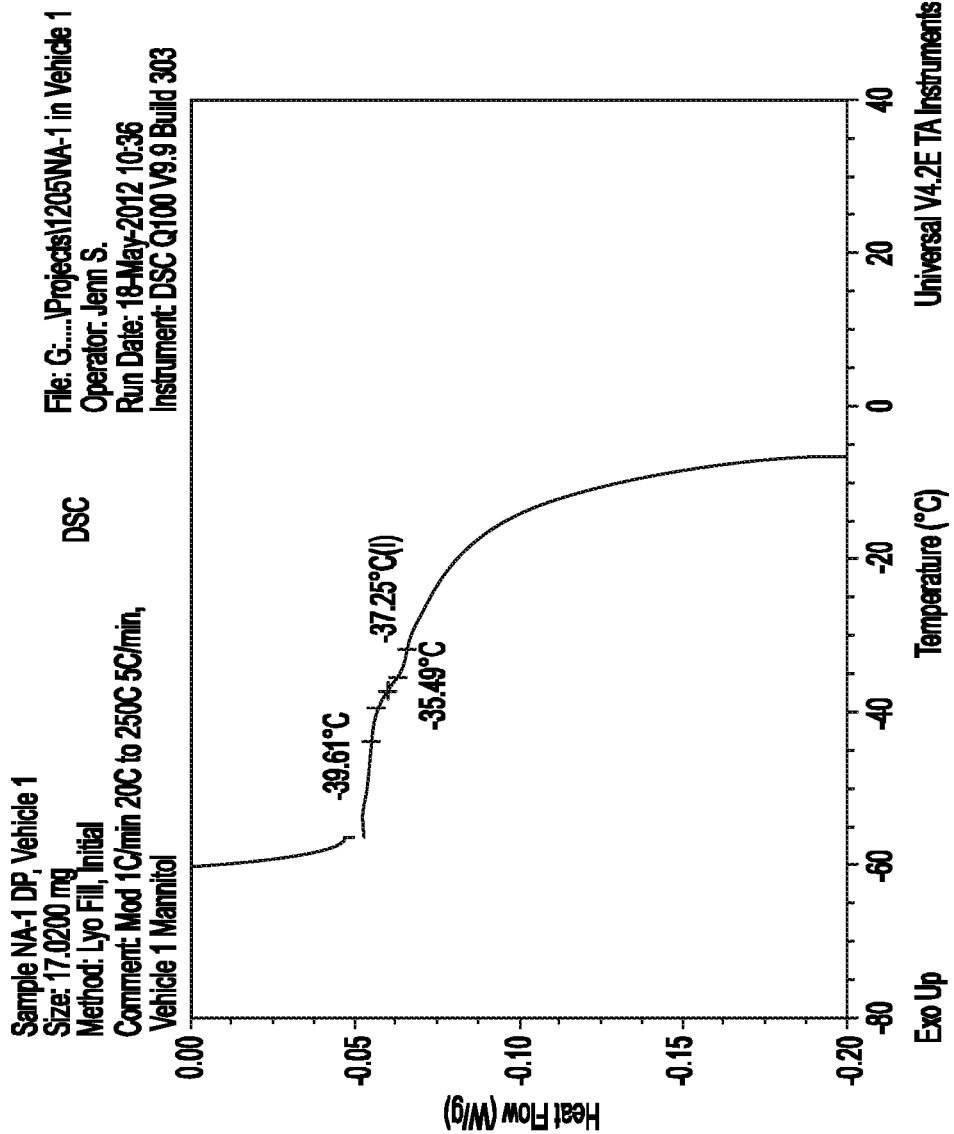
Figure 4B:
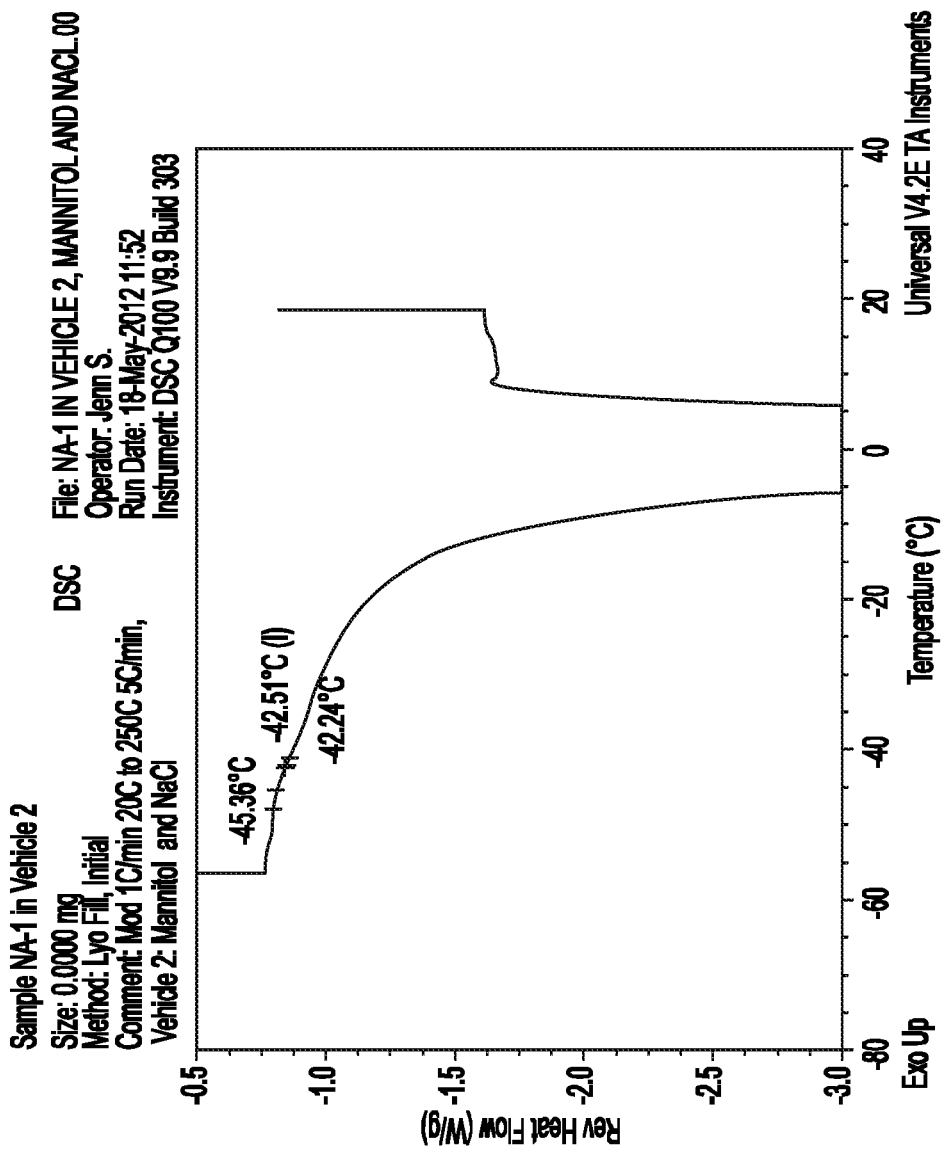

FIGS. 4A, B: Differential scanning calorimetry graphs of 20 mg/ml TAT-NR2B9c in histidine buffer pH 6.5 in the presence of Mannitol (A) or Mannitol and NaCl (B).

Figure 5A:
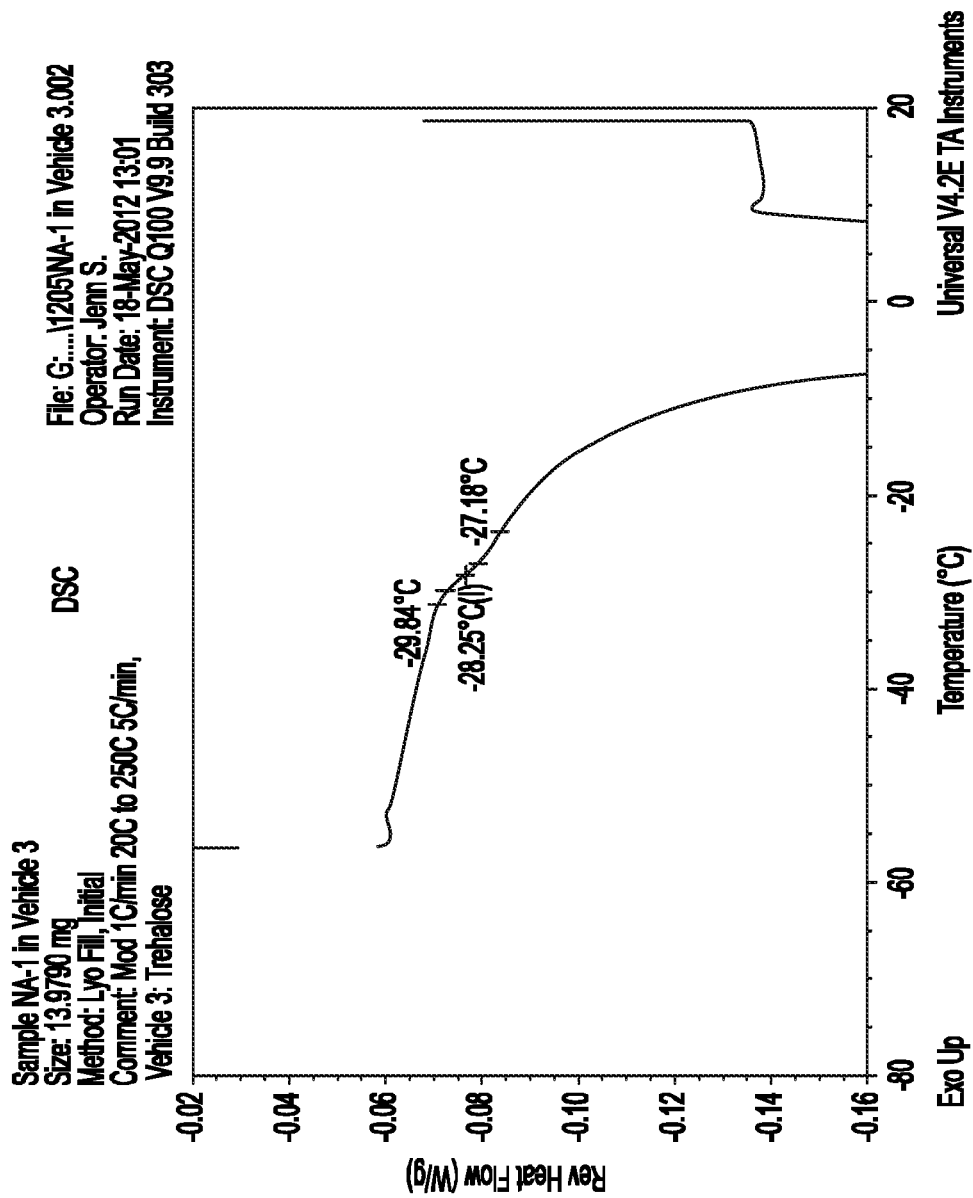
Figure 5B:
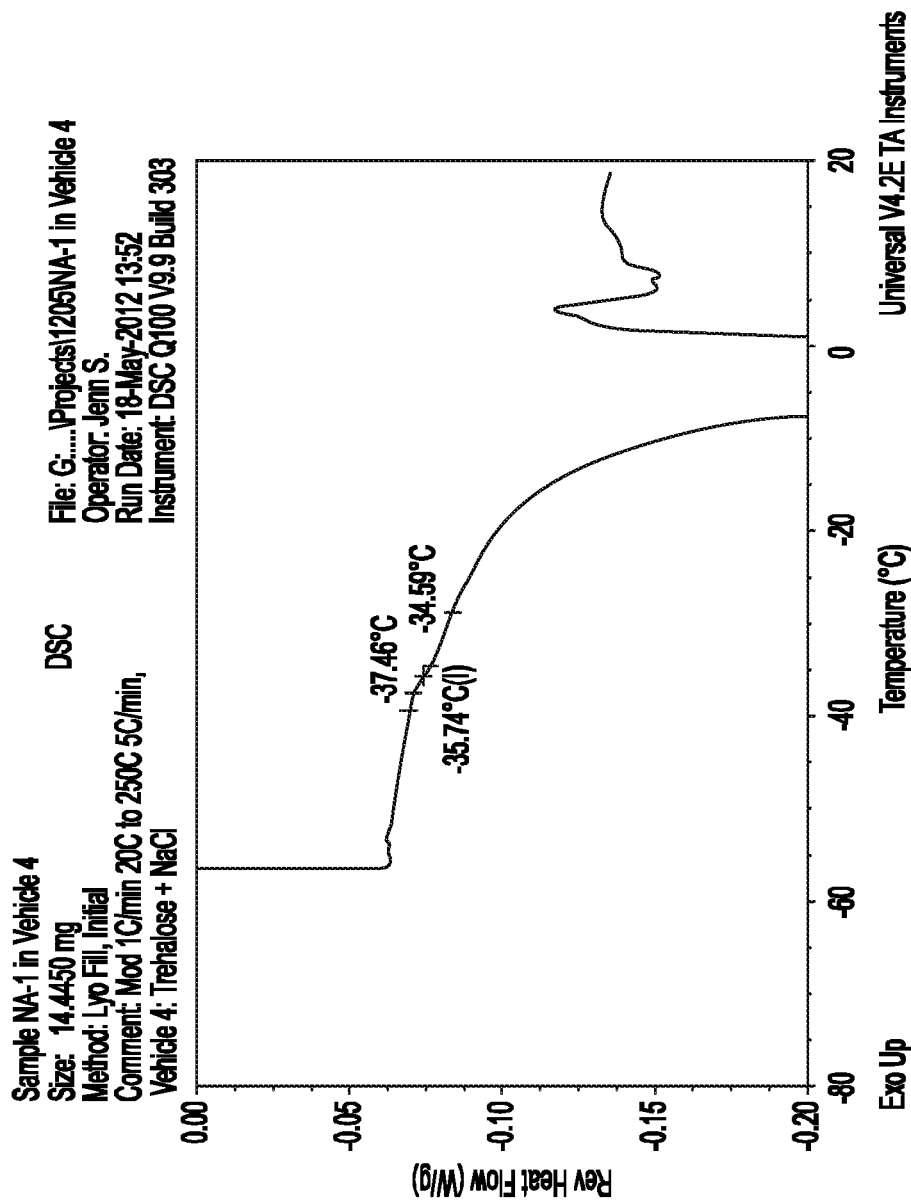

FIGS. 5A, B: Differential scanning calorimetry graphs of 20 mg/ml TAT-NR2B9c in histidine buffer pH 6.5 in the presence of Trehalose (A) or Trehalose and NaCl (B).

Figure 6A:
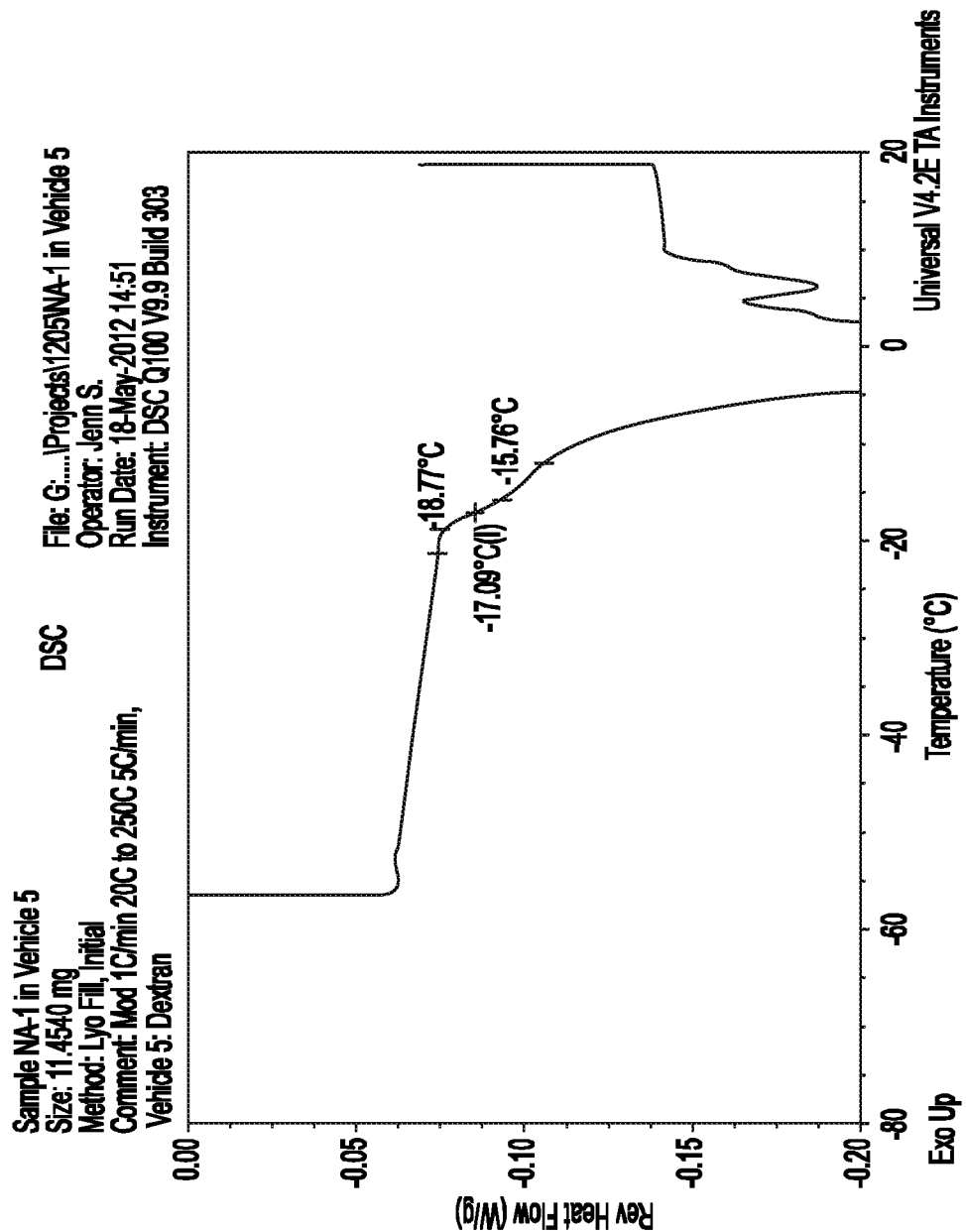
Figure 6B:
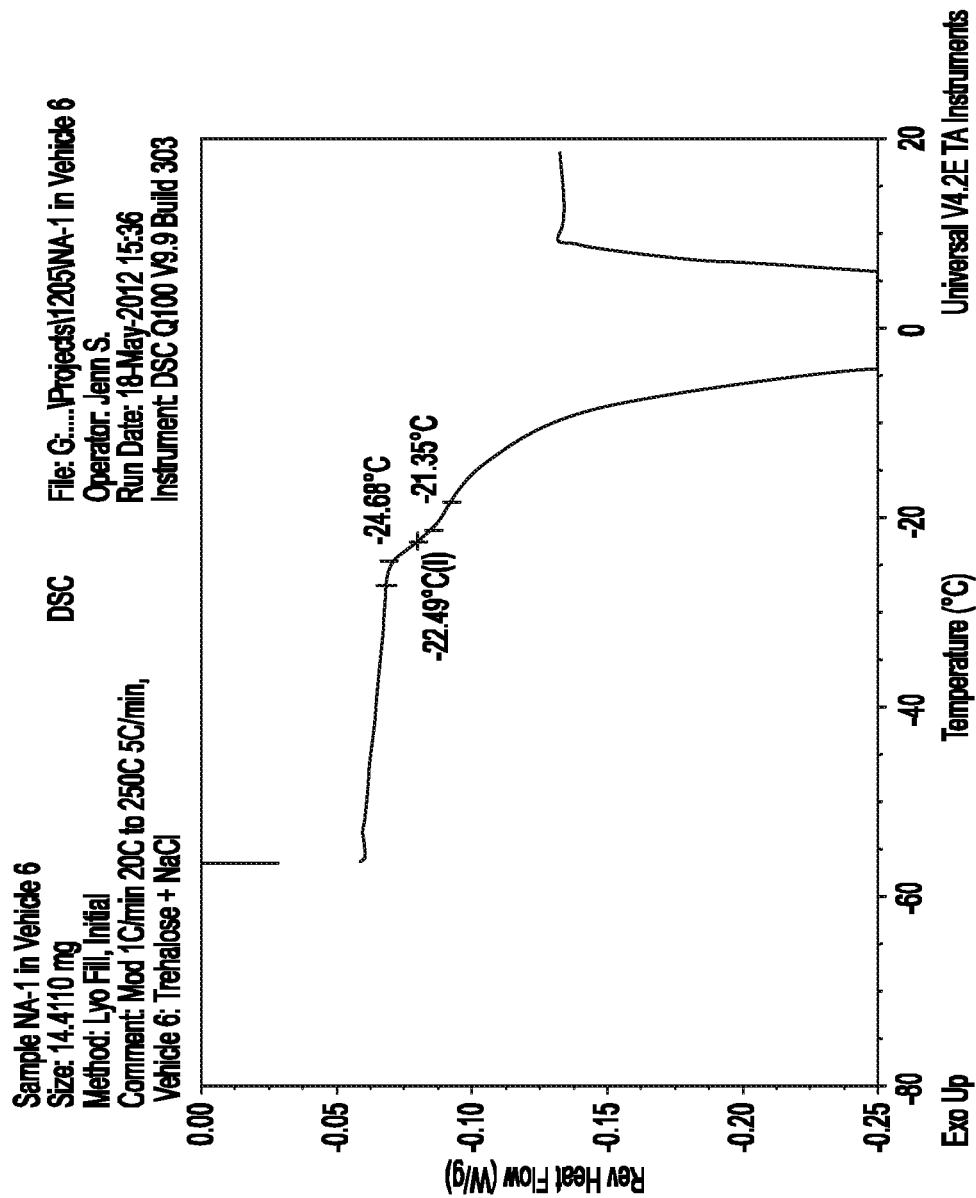

FIGS. 6A, B: Differential scanning calorimetry graph of 20 mg/ml TAT-NR2B9c in histidine buffer pH 6.5 in the presence of Dextran-40 (A) or Dextran-40 and NaCl (B).

FIGS. 7A, B: A) Cake appearance following lyophilization of 3 mL of 90 mg/ml TAT-NR2B9c in 100 mM Histidine pH 6.5 with 120 mM Trehalose. B). Cake appearance of alternative TAT-NR2B9c formulations with different amounts of histidine and trehalose.

DEFINITIONS

As well as active ingredients, lyophilized formulations can include one or more of the following classes of components. The classes are not mutually exclusive; in other words the same agent can component can fall within multiple classes.

A "bulking agent" provides structure to a freeze-dried peptide. Bulking agents include, mannitol, trehalose, dextran-40, glycine, lactose, sorbitol, and sucrose among others. In addition to providing a pharmaceutically elegant cake, bulking agents may also impart useful qualities in regard to modifying the collapse temperature, providing freeze-thaw protection, glass transition temperature and enhancing the protein stability over long-term storage. These agents can also serve as tonicity modifiers.

A buffer is an agent that maintains the solution pH in an acceptable range prior to lyophilization. A preferred buffer is histidine. Other buffers include succinate (sodium or potassium), histidine, citrate (sodium), gluconate, acetate, phosphate, Tris and the like. Preferred buffers are effective in a pH range from about 5.5 to about 7 or about 6 to about 7; preferably a pH of about 6.5. Examples of buffers that control the pH in this range include succinate (such as sodium succinate), gluconate, histidine, citrate and other organic acid buffers.

A "cryoprotectant" provides stability to a peptide against freezing-induced stresses, presumably by being preferentially excluded from the protein surface. It may also offer protection during primary and secondary drying, and long-term product storage. Examples are polymers such as dextran and polyethylene glycol; sugars (including sugar alcohols) such as sucrose, glucose, trehalose, and lactose; and surfactants such as polysorbates; and amino acids such as glycine, arginine, and serine.

A lyoprotectant provides stability to the peptide during the drying or 'dehydration' process (primary and secondary drying cycles), presumably by providing an amorphous glassy matrix and by binding with the protein through hydrogen bonding, replacing the water molecules that are removed during the drying process. This helps to maintain the peptide conformation, minimize peptide degradation during the lyophilization cycle and improve the long-term product stability. Examples include polyols or sugars such as sucrose and trehalose.

To the extent not already mentioned, other stabilizers or inhibitors of degradations can be included deamidation inhibitors, surfactants, some common ones are fatty acid esters of sorbitan polyethoxylates (e.g., polysorbate 20 or polysorbate 80), poloxamer 188, and detergents.

The terms "lyophilization," "lyophilized," and "freeze-dried" refer to a process by which the material to be dried is first frozen and then the ice or frozen solvent is removed by sublimation in a vacuum environment.

A "pharmaceutical formulation" or composition is a preparation that permits an active agent to be effective, and lacks additional components which are toxic to the subjects to which the formulation would be administered.

"Reconstitution time" is the time that is required to rehydrate a lyophilized formulation with a solution to solution which is free of particles to the naked eye.

A "stable" lyophilized peptide formulation is one with no significant changes observed at 20° C. for at least one week, month, or more preferably at least three months, at least six months or a year. Changes are considered insignificant if no more than 10%, preferably 5%, of peptide is degraded as measured by SEC-HPLC. The rehydrated solution is colorless, or clear to slightly opalescent by visual analysis. The concentration, pH and osmolality of the formulation have no more than +/−10% change after storage. Potency is within 70-130%, preferably 80-120% or sometimes 80-100% of a freshly prepared control sample. No more than 10%, preferably 5% of clipping is observed. No more than 10%, preferably 5% of aggregation is formed. Stability can be measured by various methods reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10:29-90 (1993).

The term "isotonic" means that the formulation of interest has essentially the same osmotic pressure as human blood. Isotonic formulations will generally have an osmotic pressure from about 270-328 mOsm. Slightly hypotonic pressure is 250-269 and slightly hypertonic pressure is 328-350 mOsm. Osmotic pressure can be measured, for example, using a vapor pressure or ice-freezing type osmometer.

Tonicity Modifiers: Salts (NaCl, KCl, MgCl2, CaCl2) can be used as tonicity modifiers to control osmotic pressure. In addition, cryoprotectants/lyoprotectants and/or bulking agents such as sucrose, mannitol, or glycine can serve as tonicity modifiers.

Numeric values such as concentrations or pH's are given within a tolerance reflecting the accuracy with which the value can be measured. Unless the context requires otherwise, fractional values are rounded to the nearest integer. Unless the context requires otherwise, recitation of a range of values means that any integer or subrange within the range can be used.

The terms "disease" and "condition" are used synonymously to indicate any disruption or interruption of normal structure or function in a subject.

DETAILED DESCRIPTION

I. General

Peptides synthesized by solid state methods are typically produced as trifluoroacetate salts because trifluoroacetic acid (TFA) is used for deprotection of peptides and/or removal of peptides from resins. For pharmaceutical use, the trifluoroacetate is usually replaced with acetate as a counterion because acetate is nontoxic and the replacement of trifluoroacetate by acetate is straightforward. Such has been the case for the peptide TAT-NR2B9c synthesized to-date as described in WO2010144721 or PCT/US2013/071755 WO2014/085349 and elsewhere.

Acetate is often a preferred counterion for pharmaceutically peptides because trifluoroacetate can be exchanged for acetate with a minor change in the typical purification process of a peptide resulting from solid phase synthesis in which the final wash is performed with acetic acid instead of trifluoroacetic acid followed by elution with acetonitrile. Occasionally other counterions are used instead. For example, chloride is sometimes used for poorly soluble peptides because it improves their solubility. However, conversion of trifluoride acetate or acetate to chloride results in loss of some peptide. Moreover, presence of HCl resulting from chloride exchange has been reported to modify the structure and reduce the thermal stability of some peptides (Biochemistry, 5th edition, Berg et al. eds, Freeman; 2002); J Pept Sci. 2007 January; 13(1):37-43). TAT-NR2B9c is already a highly soluble peptide as an acetate salt. Accordingly, replacement of trifluoroacetate or acetate salt with chloride would have appeared to have the disadvantages of decreased yield and possible reduced stability without any compensating benefit.

Surprisingly it has been found that a chloride salt of TAT-NR2B9c confers significantly greater stability in the lyophilized form than an acetate salt of TAT-NR2B9c in the same formulation, or an acetate salt of TAT-NR2B9c lyophilized from saline. The chloride salt can remain sufficiently stable for clinical use even with storage at summer time ambient temperatures reaching or even exceeding 37° C. for several years. The greater stability of the chloride salt over acetate more than compensates for any greater effort or reduced yield required in replacing trifluoroacetate as a salt. The present invention provides lyophilized formulations of active agents, particularly of TAT-NR2B9c as a chloride salt. Such formulations are stable at ambient temperature (e.g., at least 20° C.) thus facilitating maintenance of supplies of such a formulation in ambulances or the like or with emergency personnel for administration at the scene of illness or accident or between such scene and a medical facility.

Lyophilized formulations are prepared from a prelyophilized formulation comprising an active agent, a buffer, a bulking agent and water. Other components, such as cryo or lyopreservatives, a tonicity agent pharmaceutically acceptable carriers and the like may or may not be present. A preferred active agent is a chloride salt of TAT-NR2B9c. A preferred buffer is histidine. A preferred bulking agent is trehalose. Trehalose also serves as a cryo and lyo-preservative. An exemplary prelyophilized formulation comprises the active agent (e.g., chloride salt of TAT-NR2B9c), histidine (10-100 mM, 15-100 mM 15-80 mM, 40-60 mM or 15-60 mM, for example, 20 mM or optionally 50 mM, or 20-50 mM)) and trehalose (50-200 mM, preferably 80-160 mM, 100-140 mM, more preferably 120 mM). The pH is 5.5 to 7.5, more preferably, 6-7, more preferably 6.5. The concentration of active agent (e.g., chloride salt of TAT-NR2B9c) is 20-200 mg/ml, preferably 50-150 mg/ml, more preferably 70-120 mg/ml or 90 mg/ml. Thus, an exemplary prelyophilized formulation is 20 mM histidine, 120 mM trehalose, and 90 mg/ml chloride salt of TAT-NR2B9c. Optionally an acetylation scavenger, such as lysine can be included, as described in co-pending application US20170112769, to further reduce any residual acetate or trifluoroacetate in the formulation.

After lyophilization, lyophilized formulations have a low-water content, preferably from about 0%-5% water, more preferably below 2.5% water by weight. Lyophilized formulations can be stored in a freezer (e.g., -20 or -70° C.), in a refrigerator (0-4° C.) or at room temperature (20-25° C.).

Active agents are reconstituted in an aqueous solution, preferably water for injection or optionally normal saline (0.8-1.0% saline and preferably 0.9% saline). Reconstitution can be to the same or a smaller or larger volume than the prelyophilized formulation. Preferably, the volume is larger post-reconstitution than before (e.g., 3-6 times larger). For example, a prelyophilization volume of 3-5 ml can be reconstituted as a volume of 10 mL, 12 mL, 13.5 ml, 15 mL or 20 mL or 10-20 mL among others. After reconstitution, the concentration of histidine is preferably 2-20 mM, e.g., 2-7 mM, 4.0-6.5 mM, 4.5 mM or 6 mM; the concentration of trehalose is preferably 15-45 mM or 20-40 mM or 25-27 mM or 35-37 mM. The concentration of lysine is preferably 100-300 mM, e.g., 150-250 mM, 150-170 mM or 210-220 mM. The active agent is preferably at a concentration of 10-30 mg/ml, for example 15-30, 18-20, 20 mg/ml of active agent (e.g., TAT-NR2B9c) or 25-30, 26-28 or 27 mg/mL active agent. An exemplary formulation after reconstitution has 4-5 mM histidine, 26-27 mM trehalose, 150-170 mM lysine and 20 mg/ml TAT-NR2B9c (with concentrations rounded to the nearest integer). A second exemplary formulation after reconstitution has 5-7 mM histidine, 35-37 mM trehalose, 210-220 mM lysine and 26-28 mg/ml TAT-NR2B9c (with concentrations rounded to the nearest integer). The reconstituted formulation can be further diluted before administration such as by adding into a fluid bag containing normal saline for intravenous infusion.

Any description of a formulation as comprising or including (or similar terminology) specified components should be understood as alternatively or additional describing a formulation consisting of or consisting essentially of those specified components.

Methods of freeze drying are set forth, for example, in Methods in Enzymology, Vol. 22, Pages 33-39, Academic Press, New York (1971); and in Freeze-Drying, E. W. Flosdorf, Rheinhold, New York (1949). TAT-NR2B9c is preferably lyophilized in the same vial as that in which it will be reconstituted for use. An aqueous solution of TAT-NR2B9c is added to the vial optionally after filtering through a sterilizing filtration system, such as a 0.22 micron filter standardly used for peptides. Formulations can be lyophilized in a controlled cycle, such as described in the Examples. A prelyophilized formulation can be placed in a vial, and lyophilized at reduced temperature and pressure. After lyophilization, vials can be sealed. For use, the lyophilizate is reconstituted with water for injection, normal saline or other pharmaceutically acceptable carrier or diluent.

A variety of containers are suitable for lyophilization. A container should be able to withstand the outside pressure when the container is sealed and stored under partial vacuum. The container should be made of a material that allows a reasonable transfer of heat from outside to inside. The size of the container should be such that the solution to be lyophilized occupies not more than 20% of the useful volume or may be overfilled with an excess, in accord with then-prevailing USP recommendations for the volume in a container. For example, a 0.5 ml solution may be filled in a 3 ml vial. The vials may be made of glass e.g. borosilicate, or plastic, e.g. polypropylene.

Glass bottles commonly used for lyophilizing biological materials can be used. Another suitable container is a two-compartment syringe wherein one compartment contains the lyophilized TAT-NR2B9c peptide cake and the other compartment contains the aqueous diluent. After lyophilization is complete, the vacuum within the vials or ampules may be released by filling the system with an inert gas, stoppered in place using standard equipment and then crimp sealed. Such a method will ensure a sterile final product. Other two-part solutions such as a bag with a breakable seal between the lyophilized drug compartment and the diluent can be used as well.

II. Active Agents

Although much of the description refers to the active agent TAT-NR2B9c for purposes of exemplification, other active agents as described below can be prepared as chloride salts or formulated according to the principles described for TAT-NR2B9c. Specific concentrations given for TAT-NR2B9c can be used as is for other agents or converted to give equimolar concentrations of the other agent and TAT-NR2B9c.

Active agents inhibit interaction between PSD-95 and one or more NMDARs (e.g., 2A, 2B, 2C or 2D) or nNOS (e.g., Swiss-Prot P29475) by binding to PSD-95. Such agents are useful for reducing one or more damaging effects of stroke and other neurological conditions mediated at least in part by NMDAR excitotoxicity. Such agents include peptides having an amino acid sequence including or based on the PL motif of a NMDA Receptor or PDZ domain of PSD-95. Such peptides can also inhibit interactions between PSD-95 and nNOS and other glutamate receptors (e.g., kainite receptors or AMPA receptors), such as KV1.4 and GluR6. Preferred peptides inhibit interaction between PDZ domains 1 and 2 of postsynaptic density-95 protein (PSD-95)(human amino acid sequence provided by Stathakism, Genomics 44(1):71-82 (1997)) and the C-terminal PL sequence of one or more NMDA Receptor 2 subunits including the NR2B subunit of the neuronal N-methyl-D-aspartate receptor (Mandich et al., Genomics 22, 216-8 (1994)). NMDAR2B has GenBank ID 4099612, a C-terminal 20 amino acids FNGSSNGHVYEKLSSIESDV (SEQ ID NO:11) and a PL motif ESDV (SEQ ID NO:12). Preferred peptides inhibit the human forms of PSD-95 and human NMDAR receptors. However, inhibition can also be shown from species variants of the proteins. A list of NMDA and glutamate receptors that can be used appears below:

| Name | GI or Acc# | C-terminal 20 mer sequence | C-terminal 4 mer sequence | PL? | internal PL ID |
|---|---|---|---|---|---|
| | | NMDA Receptors With PL Sequences | | | |
| NMDAR1 | 307302 | HPTDITGPLNLSDPSVSTVV (SEQ ID NO: 13) | STVV (SEQ ID NO: 27) | X | AA216 |
| NMDAR1-1 | 292282 | HPTDITGPLNLSDPSVSTVV (SEQ ID NO: 13) | STVV (SEQ ID NO: 27) | X | AA216 |
| NMDAR1-4 | 472845 | HPTDITGPLNLSDPSVSTVV (SEQ ID NO: 13) | STVV (SEQ ID NO: 27) | X | AA216 |
| NMDAR1-3b | 2343286 | HPTDITGPLNLSDPSVSTVV (SEQ ID NO: 13) | STVV (SEQ ID NO: 27) | X | AA216 |
| NMDAR1-4b | 2343288 | HPTDITGPLNLSDPSVSTVV (SEQ ID NO: 13) | STVV (SEQ ID NO: 27) | X | AA216 |
| NMDAR1-2 | 11038634 | RRAIEREEGQLQLCSRHRES (SEQ ID NO: 14) | HRES (SEQ ID NO: 28) | | |
| NMDAR1-3 | 11038636 | RRAIEREEGQLQLCSRHRES (SEQ ID NO: 14) | HRES (SEQ ID NO: 28) | | |
| NMDAR2C | 6006004 | TQGFPGPCTWRRISSLESEV (SEQ ID NO: 15) | ESEV (SEQ ID NO: 29) | X | AA180 |
| NMDAR3 | 560546 | FNGSSNGHVYEKLSSIESDV (SEQ ID NO: 11) | ESDV (SEQ ID NO: 12) | X | AA34.1 |
| NMDAR3A | 17530176 | AVSRKTELEEYQRTSRTCES (SEQ ID NO: 16) | TCES (SEQ ID NO: 30) | | |
| NMDAR2B | 4099612 | FNGSSNGHVYEKLSSIESDV (SEQ ID NO: 11) | ESDV (SEQ ID NO: 12) | X | |
| NMDAR2A | 558748 | LNSCSNRRVYKKMPSIESDV (SEQ ID NO: 17) | ESDV (SEQ ID NO: 12) | X | AA34.2 |
| NMDAR2D | 4504130 | GGDLGTRRGSAHFSSLESEV (SEQ ID NO: 18) | ESEV (SEQ ID NO: 29) | X | |
| Glutamate receptor delta 2 | AF009014 | QPTPTLGLNLGNDPDRGTSI (SEQ ID NO: 19) | GTSI (SEQ ID NO: 31) | X | |
| Glutamate receptor 1 | I28953 | MQSIPCMSHSSGMPLGATGL (SEQ ID NO: 20) | ATGL (SEQ ID NO: 32) | X | |
| Glutamate receptor 2 | L20814 | QNFATYKEGYNVYGIESVKI (SEQ ID NO: 21) | SVKI (SEQ ID NO: 33) | X | |

NMDA Receptors With PL Sequences (continued)

| Name | GI or Acc# | C-terminal 20 mer sequence | C-terminal 4 mer sequence | PL? | internal PL ID |
|---|---|---|---|---|---|
| Glutamate receptor 3 | AF167332 | QNYATYREGYNVYG1ESVKI (SEQ ID NO: 22) | SVKI (SEQ ID NO: 33) | X | |
| Glutamate receptor 4 | U16129 | HTGTAIRQSSGLAVIASDLP (SEQ ID NO: 23) | SDLP (SEQ ID NO: 34) | | |
| Glutamate receptor 5 | U16125 | SFTSILTCHQRRTQRKETVA (SEQ ID NO: 24) | ETVA (SEQ ID NO: 35) | X | |
| Glutamate receptor 6 | U16126 | EVINMHTFNDRRLPGKETMA (SEQ ID NO: 25) | ETMA (SEQ ID NO: 36) | X | |

Peptides can include or be based on a PL motif from the C-terminus of any of the above subunits and have an amino acid sequence comprising [S/T]-X-[V/L]. This sequence preferably occurs at the C-terminus of the peptides of the invention. Preferred peptides have an amino acid sequence comprising [E/D/N/Q]-[S/T]-[D/E/Q/N]-[V/L] (SEQ ID NO:38) at their C-terminus. Exemplary peptides comprise: ESDV (SEQ ID NO:12), ESEV (SEQ ID NO:29), ETDV (SEQ ID NO:39), ETEV (SEQ ID NO:40), DTDV (SEQ ID NO:41), and DTEV (SEQ ID NO:42) as the C-terminal amino acids. Two particularly preferred peptides are KLSSIESDV (SEQ ID NO:5), and KLSSIETDV (SEQ ID NO:43). Such peptides usually have 3-25 amino acids (without an internalization peptide), peptide lengths of 5-10 amino acids, and particularly 9 amino acids (also without an internalization peptide) are preferred. In some such peptides, all amino acids are from the C-terminus of an NMDA receptor (not including amino acids from an internalization peptide).

Peptides and peptidomimetics of the invention can contain modified amino acid residues for example, residues that are N-alkylated. N-terminal alkyl modifications can include e.g., N-Methyl, N-Ethyl, N-Propyl, N-Butyl, N-Cyclohexylmethyl, N-Cyclyhexylethyl, N-Benzyl, N-Phenylethyl, N-phenylpropyl, N-(3, 4-Dichlorophenyl)propyl, N-(3,4-Difluorophenyl)propyl, and N-(Naphthalene-2-yl)ethyl).

Bach, J. Med. Chem. 51, 6450-6459 (2008) and WO 2010/004003 have described a series of analogs of NR2B9c (SEQ ID NO:6). PDZ-binding activity is exhibited by peptides having only three C-terminal amino acids (SDV). Bach also reports analogs having an amino acid sequence comprising or consisting of $X_1tSX_2V$ (SEQ ID NO:68), wherein t and S are alternative amino acids, $X_1$ is selected from among E, Q, and A, or an analogue thereof, $X_2$ is selected from among A, Q, D, N, N-Me-A, N-Me-Q, N-Me-D, and N-Me-N or an analog thereof. Optionally the peptide is N-alkylated in the P3 position (third amino acid from C-terminus, i.e. position occupied by tS). The peptide can be N-alkylated with a cyclohexane or aromatic substituent, and further comprises a spacer group between the substituent and the terminal amino group of the peptide or peptide analogue, wherein the spacer is an alkyl group, preferably selected from among methylene, ethylene, propylene and butylene. The aromatic substituent can be a naphthalen-2-yl moiety or an aromatic ring substituted with one or two halogen and/or alkyl group.

Other modifications can also be incorporated without adversely affecting the activity and these include substitution of one or more of the amino acids in the natural L-isomeric form with amino acids in the D-isomeric form. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, generally referred to as the D-amino acid, but which can additionally be referred to as the R- or S-form. Thus, a peptidomimetic may include 1, 2, 3, 4, 5, at least 50%, or all D-amino acid resides. A peptidomimetic containing some or all D residues is sometimes referred to an "inverso" peptide.

Peptidomimetics also include retro peptides. A retro peptide has a reverse amino acid sequence. Peptidomimetics also include retro inverso peptides in which the order of amino acids is reversed from so the originally C-terminal amino acid appears at the N-terminus and D-amino acids are used in place of L-amino acids. WO 2008/014917 describes a retro-inverso analog of Tat-NR2B9c having the amino acid sequence vdseisslk-rrrqrrkkrgyin (SEQ ID NO:69) (lower case letters indicating D amino acids), and reports it to be effective inhibiting cerebral ischemia. Another effective peptide described herein is Rv-Tat-NR2B9c (RRRQRRKKR-GYKLSSIESDV; SEQ ID NO:70).

A linker, e.g., a polyethylene glycol linker, can be used to dimerize the active moiety of the peptide or the peptidomimetic to enhance its affinity and selectivity towards proteins containing tandem PDZ domains. See e.g., Bach et al., (2009) Angew. Chem. Int. Ed. 48:9685-9689 and WO 2010/004003. A PL motif-containing peptide is preferably dimerized via joining the N-termini of two such molecules, leaving the C-termini free. Bach further reports that a pentamer peptide IESDV (SEQ ID NO:71) from the C-terminus of NMDAR 2B was effective in inhibiting binding of NMDAR 2B to PSD-95. IETDV (SEQ ID NO:73) can also be used instead of IESDV (SEQ ID NO:71). Optionally, about 2-10 copies of a PEG can be joined in tandem as a linker. Optionally, the linker can also be attached to an internalization peptide or lipidated to enhance cellular uptake. Examples of illustrative dimeric inhibitors are shown below (see Bach et al., PNAS 109 (2012) 3317-3322). Any of the PSD-95 inhibitors disclosed herein can be used instead of IETDV (SEQ ID NO:71), and any internalization peptide or lipidating moiety can be used instead of tat. Other linkers to that shown can also be used.

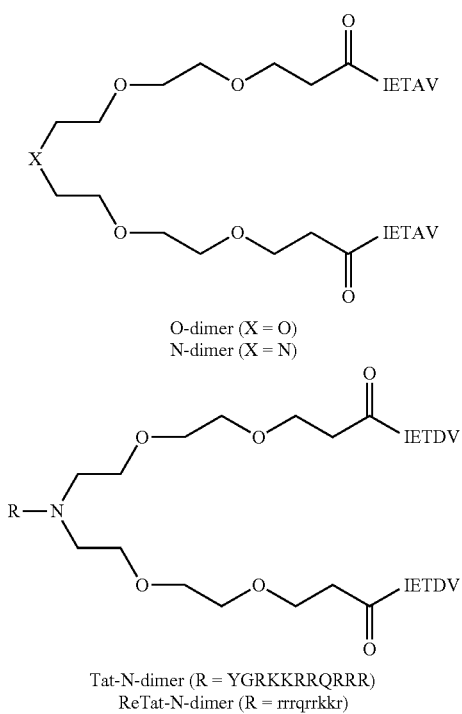

IETAV is assigned SEQ ID NO:26, YGRKKRRQRRR SEQ ID NO:2, and rrrqrrkkr, SEQ ID NO:10, lower case letters indicated D-amino acids.

Appropriate pharmacological activity of peptides, peptidomimetics or other agent can be confirmed if desired, using previously described rat models of stroke before testing in the primate and clinical trials described in the present application. Peptides or peptidomimetics can also be screened for capacity to inhibit interactions between PSD-95 and NMDAR 2B using assays described in e.g., U.S. 20050059597, which is incorporated by reference. Useful peptides typically have IC50 values of less than 50 µM, 25 µM, 10 µM, 0.1 µM or 0.01 µM in such an assay. Preferred peptides typically have an IC50 value of between 0.001-1 and more preferably 0.001-0.05, 0.05-0.5 or 0.05 to 0.1 µM. When a peptide or other agent is characterized as inhibiting binding of one interaction, e.g., PSD-95 interaction to NMDAR2B, such description does not exclude that the peptide or agent also inhibits another interaction, for example, inhibition of PSD-95 binding to nNOS.

Peptides such as those just described can optionally be derivatized (e.g., acetylated, phosphorylated, myristoylated, geranylated, pegylated and/or glycosylated) to improve the binding affinity of the inhibitor, to improve the ability of the inhibitor to be transported across a cell membrane or to improve stability. As a specific example, for inhibitors in which the third residue from the C-terminus is S or T, this residue can be phosphorylated before use of the peptide.

A pharmacological agent can be linked to an internalization peptide to facilitate uptake into cells and/or across the blood brain barrier. Internalization peptides are a well-known class of relatively short peptides that allow many cellular or viral proteins to traverse membranes. Internalization peptides, also known as cell membrane transduction peptides or cell penetrating peptides can have e.g., 5-30 amino acids. Such peptides typically have a cationic charge from an above normal representation (relative to proteins in general) of arginine and/or lysine residues that is believed to facilitate their passage across membranes. Some such peptides have at least 5, 6, 7 or 8 arginine and/or lysine residues. Examples include the antennapedia protein (Bonfanti, Cancer Res. 57, 1442-6 (1997)) (and variants thereof), the tat protein of human immunodeficiency virus, the protein VP22, the product of the UL49 gene of herpes simplex virus type 1, Penetratin, SynB1 and 3, Transportan, Amphipathic, gp41NLS, polyArg, and several plant and bacterial protein toxins, such as ricin, abrin, modeccin, diphtheria toxin, cholera toxin, anthrax toxin, heat labile toxins, and *Pseudomonas aeruginosa* exotoxin A (ETA). Other examples are described in the following references (Temsamani, Drug Discovery Today, 9(23):1012-1019, 2004; De Coupade, Biochem J., 390:407-418, 2005; Saalik Bioconjugate Chem. 15: 1246-1253, 2004; Zhao, Medicinal Research Reviews 24(1):1-12, 2004; Deshayes, Cellular and Molecular Life Sciences 62:1839-49, 2005); Gao, ACS Chem. Biol. 2011, 6, 484-491, SG3 (RLSGMNEVLSFRWL (SEQ ID NO:9)), Stalmans PLoS ONE 2013, 8(8) e71752, 1-11 and supplement; Figueiredo et al., IUBMB Life 66, 182-194 (2014); Copolovici et al., ACS Nano, 8, 1972-94 (2014); Lukanowski Biotech J. 8, 918-930 (2013); Stockwell, Chem. Biol. Drug Des. 83, 507-520 (2014); Stanzl et al. Accounts. Chem. Res/46, 2944-2954 (2013); (all incorporated by reference).

A preferred internalization peptide is tat from the HIV virus. A tat peptide reported in previous work comprises or consists of the standard amino acid sequence YGRKKRRQRRR (SEQ ID NO:2) found in HIV Tat protein. If additional residues flanking such a tat motif are present (beside the pharmacological agent) the residues can be for example natural amino acids flanking this segment from a tat protein, spacer or linker amino acids of a kind typically used to join two peptide domains, e.g., gly (ser)$_4$ (SEQ ID NO:44), TGEKP (SEQ ID NO:45), GGRRGGGS (SEQ ID NO:46), or LRQRDGERP (SEQ ID NO:47) (see, e.g., Tang et al. (1996), J. Biol. Chem. 271, 15682-15686; Hennecke et al. (1998), Protein Eng. 11, 405-410)), or can be any other amino acids that do not significantly reduce capacity to confer uptake of the variant without the flanking residues. Preferably, the number of flanking amino acids other than an active peptide does not exceed ten on either side of YGRKKRRQRRR (SEQ ID NO:2). One suitable tat peptide comprising additional amino acid residues flanking the C-terminus of YGRKKRRQRRR (SEQ ID NO:2) is YGRKKRRQRRRPQ (SEQ ID NO:48). However, preferably, no flanking amino acids are present. Other tat peptides that can be used include GRKKRRQRRRPQ (SEQ ID NO:4) and GRKKRRQRRRP (SEQ ID NO:72).

Variants of the above tat peptide having reduced capacity to bind to N-type calcium channels are described by WO/2008/109010. Such variants can comprise or consist of an amino acid sequence XGRKKRRQRRR (SEQ ID NO:49), in which X is an amino acid other than Y or nothing (in which case G is a free N-terminal residue). A preferred tat peptide has the N-terminal Y residue substituted with F. Thus, a tat peptide comprising or consisting of FGRKKRRQRRR (SEQ ID NO:3) is preferred. Another preferred variant tat peptide consists of GRKKRRQRRR (SEQ ID NO:1). Another preferred tat peptide comprises or consists of RRRQRRKKRG or RRRQRRKKRGY (amino acids 1-10 or 1-11 of SEQ ID NO:70). Other t at derived peptides that facilitate uptake of a pharmacological agent without inhibiting N-type calcium channels include those presented below.

```
X-FGRKKRRQRRR (F-Tat) (SEQ ID NO: 8)

X-GKKKKKQKKK (SEQ ID NO: 50)

X-RKKRRQRRR (SEQ ID NO: 51)

X-GAKKRRQRRR (SEQ ID NO: 52)

X-AKKRRQRRR (SEQ ID NO: 53)

X-GRKARRQRRR (SEQ ID NO: 54)

X-RKARRQRRR (SEQ ID NO: 55)

X-GRKKARQRRR (SEQ ID NO: 56)

X-RKKARQRRR (SEQ ID NO: 57)

X-GRKKRRQARR (SEQ ID NO: 58)

X-RKKRRQARR (SEQ ID NO: 59)

X-GRKKRRQRAR (SEQ ID NO: 60)

X-RKKRRQRAR (SEQ ID NO: 61)

X-RRPRRPRRPRR (SEQ ID NO: 62)

X-RRARRARRARR (SEQ ID NO: 63)

X-RRRARRRARR (SEQ ID NO: 64)

X-RRRPRRRPRR (SEQ ID NO: 65)

X-RRPRRPRR (SEQ ID NO: 66)

X-RRARRARR (SEQ ID NO: 67)
```

X can represent a free amino terminus, one or more amino acids, or a conjugated moiety. Internalization peptides can be used in inverso or retro or inverso retro form with or without the linked peptide or peptidomimetic being in such form. For example, a preferred chimeric peptide has an amino acid sequence comprising or consisting of YGRKKRRQRRR-KLSSIESDV (SEQ ID NO:6, also known as TAT-NR2B9c or Tat-NR2B9c), or YGRKKRRQRRR-KLSSIETDV (SEQ ID NO:7). Other preferred chimeric peptides differ from SEQ ID NO:6 or NO:7 by up to 1, 2, 3, 4 or 5 amino acid substitutions, deletions or additions (internal or at the ends). Other preferred peptides include RRRQRRKKRGY-KLSSIESDV (SEQ ID NO:70, also known as RvTat-NR2B9c or having an amino acid sequence comprising or consisting of RRRQRRKKRGY-KLSSIETDV (SEQ ID NO:37).

Internalization peptides can be attached to pharmacological agents by conventional methods. For example, the agents can be joined to internalization peptides by chemical linkage, for instance via a coupling or conjugating agent. Numerous such agents are commercially available and are reviewed by S. S. Wong, Chemistry of Protein Conjugation and Cross-Linking, CRC Press (1991). Some examples of cross-linking reagents include J-succinimidyl 3-(2-pyridyldithio) propionate (SPDP) or N,N'-(1,3-phenylene) bismaleimide; N,N'-ethylene-bis-(iodoacetamide) or other such reagent having 6 to 11 carbon methylene bridges (which relatively specific for sulfhydryl groups); and 1,5-difluoro-2,4-dinitrobenzene (which forms irreversible linkages with amino and tyrosine groups). Other cross-linking reagents include p,p'-difluoro-m, m'-dinitrodiphenylsulfone (which forms irreversible cross-linkages with amino and phenolic groups); dimethyl adipimidate (which is specific for amino groups); phenol-1,4-disulfonylchloride (which reacts principally with amino groups); hexamethylenediisocyanate or diisothiocyanate, or azophenyl-p-diisocyanate (which reacts principally with amino groups); glutaraldehyde (which reacts with several different side chains) and disdiazobenzidine (which reacts primarily with tyrosine and histidine).

For pharmacological agents that are peptides attachment to an internalization peptide can be achieved by generating a fusion protein comprising the peptide sequence fused, preferably at its N-terminus, to an internalization peptide.

Instead of or as well as linking a peptide (or other agent) inhibiting PSD-95 to an internalization peptide, such a peptide can be linked to a lipid (lipidation) to increase hydrophobicity of the conjugate relative to the peptide alone and thereby facilitate passage of the linked peptide across cell membranes and/or across the brain barrier. Lipidation is preferably performed on the N-terminal amino acid but can also be performed on internal amino acids, provided the ability of the peptide to inhibit interaction between PSD-95 and NMDAR 2B is not reduced by more than 50%. Preferably, lipidation is performed on an amino acid other than one of the four most C-terminal amino acids. Lipids are organic molecules more soluble in ether than water and include fatty acids, glycerides and sterols. Suitable forms of lipidation include myristoylation, palmitoylation or attachment of other fatty acids preferably with a chain length of 10-20 carbons, such as lauric acid and stearic acid, as well as geranylation, geranylgeranylation, and isoprenylation. Lipidations of a type occurring in posttranslational modification of natural proteins are preferred. Lipidation with a fatty acid via formation of an amide bond to the alpha-amino group of the N-terminal amino acid of the peptide is also preferred. Lipidation can be by peptide synthesis including a prelipidated amino acid, be performed enzymatically in vitro or by recombinant expression, by chemical crosslinking or chemical derivatization of the peptide. Amino acids modified by myristoylation and other lipid modifications are commercially available.

Lipidation preferably facilitates passage of a linked peptide (e.g., KLSSIESDV (SEQ ID NO:5), or KLSSIETDV (SEQ ID NO:43)) across a cell membrane and/or the blood brain barrier without causing a transient reduction of blood pressure as has been found when a standard t at peptide is administered at high dosage (e.g., at or greater than 3 mg/kg), or at least with smaller reduction that than the same peptide linked to a standard tat peptide.

Pharmacologic peptides, optionally fused to tat peptides, can be synthesized by solid phase synthesis or recombinant methods. Peptidomimetics can be synthesized using a variety of procedures and methodologies described in the scientific and patent literature, e.g., Organic Syntheses Collective Volumes, Gilman et al. (Eds) John Wiley & Sons, Inc., NY, al-Obeidi (1998) Mol. Biotechnol. 9:205-223; Hruby (1997) Curr. Opin. Chem. Biol. 1:114-119; Ostergaard (1997) Mol. Divers. 3:17-27; Ostresh (1996) Methods Enzymol. 267:220-234.

III. Salts

Peptides of the type described above are typically made by solid state synthesis. Because solid state synthesis uses trifluoroacetate (TFA) to remove protecting groups or remove peptides from a resin, peptides are typically initially produced as trifloroacetate salts. The trifluoroacetate can be replaced with another anion by for example, binding the peptide to a solid support, such as a column, washing the column to remove the existing counterion, equilibrating the column with a solution containing the new counterion and then eluting the peptide, e.g., by introducing a hydrophobic solvent such as acetonitrile into the column. Replacement of trifluoroacetate with acetate can be done with an acetate wash as the last step before peptide is eluted in an otherwise conventional solid state synthesis. Replacing trifluoroacetate or acetate with chloride can be done with a wash with ammonium chloride followed by elution. Use of a hydrophobic support is preferred and preparative reverse phase HPLC is particularly preferred for the ion exchange. Trifluoroacetate can be replaced with chloride directly or can first be replaced by acetate and then the acetate replaced by chloride.

Counterions, whether trifluoroacetate, acetate or chloride, bind to positively charged atoms on TAT-NR2B9c, particularly the N-terminal amino group and amino side chains arginine and lysine residues. Although practice of the invention, it is not dependent on understanding the exact stochiometery of peptide to anion in a salt of TAT-NR2B9c, it is believed that up to about 9 counterion molecules are present per molecule of salt.

Although replacement of one counterion by another takes place efficiently, the purity of the final counterion may be less than 100%. Thus, reference to a chloride salt of TAT-NR2B9c or other active agent means that in a preparation of the salt, chloride is the predominant anion by weight (or moles) over all other anions present in the aggregate in the salt. In other words, chloride constitutes greater than 50% and preferably greater than 75%, 95%, 99%, 99.5% or 99.9% by weight or moles of the all anions present in the salt. In such a salt or formulation prepared from the salt, acetate and trifluoroacetate in combination and individually constitutes less than 50%, 25%, 5%, 0.5% or 0.1% of the anions in the salt or formulation.

IV. Diseases

The lyophilized formulations are useful in treating a variety of diseases, particularly neurological diseases, and especially diseases mediated in part by excitotoxity. Such diseases and conditions include stroke, epilepsy, hypoxia, subarachnoid hemorrhage, traumatic injury to the CNS not associated with stroke such as traumatic brain injury and spinal cord injury, other cerebral ischemia, Alzheimer's disease and Parkinson's disease. Other neurological diseases treatable by agents of the invention not known to be associated with excitotoxicity include anxiety and pain.

A stroke is a condition resulting from impaired blood flow in the CNS regardless of cause. Potential causes include embolism, hemorrhage and thrombosis. Some neuronal cells die immediately as a result of impaired blood flow. These cells release their component molecules including glutamate, which in turn activates NMDA receptors, which raise intracellular calcium levels, and intracellular enzyme levels leading to further neuronal cell death (the excitotoxicity cascade). The death of CNS tissue is referred to as infarction. Infarction Volume (i.e., the volume of dead neuronal cells resulting from stroke in the brain) can be used as an indicator of the extent of pathological damage resulting from stroke. The symptomatic effect depends both on the volume of an infarction and where in the brain it is located. Disability index can be used as a measure of symptomatic damage, such as the Rankin Stroke Outcome Scale (Rankin, Scott Med J; 2:200-15 (1957)) and the Barthel Index. The Rankin Scale is based on assessing directly the global conditions of a patient as follows.

0: No symptoms at all
1: No significant disability despite symptoms; able to carry out all usual duties and activities.
2: Slight disability; unable to carry out all previous activities but able to look after own affairs without assistance.
3: Moderate disability requiring some help, but able to walk without assistance
4: Moderate to severe disability; unable to walk without assistance and unable to attend to own bodily needs without assistance.
5: Severe disability; bedridden, incontinent, and requiring constant nursing care and attention.

The Barthel Index is based on a series of questions about the patient's ability to carry out 10 basic activities of daily living resulting in a score between 0 and 100, a lower score indicating more disability (Mahoney et al, Maryland State Medical Journal 14:56-61 (1965)).

Alternatively stroke severity/outcomes can be measured using the NIH stroke scale, available at world wide web ninds.nih.gov/doctors/NIH Stroke ScaleJBooklet.pdf.

The scale is based on the ability of a patient to carry out 11 groups of functions that include assessments of the patient's level of consciousness, motor, sensory and language functions.

An ischemic stroke refers more specifically to a type of stroke that caused by blockage of blood flow to the brain. The underlying condition for this type of blockage is most commonly the development of fatty deposits lining the vessel walls. This condition is called atherosclerosis. These fatty deposits can cause two types of obstruction. Cerebral thrombosis refers to a thrombus (blood clot) that develops at the clogged part of the vessel "Cerebral embolism" refers generally to a blood clot that forms at another location in the circulatory system, usually the heart and large arteries of the upper chest and neck. A portion of the blood clot then breaks loose, enters the bloodstream and travels through the brain's blood vessels until it reaches vessels too small to let it pass. A second important cause of embolism is an irregular heartbeat, known as arterial fibrillation. It creates conditions in which clots can form in the heart, dislodge and travel to the brain. Additional potential causes of ischemic stroke are hemorrhage, thrombosis, dissection of an artery or vein, a cardiac arrest, shock of any cause including hemorrhage, and iatrogenic causes such as direct surgical injury to brain blood vessels or vessels leading to the brain or cardiac surgery. Ischemic stroke accounts for about 83 percent of all cases of stroke.

Transient ischemic attacks (TIAs) are minor or warning strokes. In a TIA, conditions indicative of an ischemic stroke are present and the typical stroke warning signs develop. However, the obstruction (blood clot) occurs for a short time and tends to resolve itself through normal mechanisms. Patients undergoing heart surgery are at particular risk of transient cerebral ischemic attack.

Hemorrhagic stroke accounts for about 17 percent of stroke cases. It results from a weakened vessel that ruptures and bleeds into the surrounding brain. The blood accumulates and compresses the surrounding brain tissue. The two general types of hemorrhagic strokes are intracerebral hemorrhage and subarachnoid hemorrhage. Hemorrhagic stroke result from rupture of a weakened blood vessel ruptures. Potential causes of rupture from a weakened blood vessel include a hypertensive hemorrhage, in which high blood pressure causes a rupture of a blood vessel, or another underlying cause of weakened blood vessels such as a ruptured brain vascular malformation including a brain aneurysm, arteriovenous malformation (AVM) or cavernous malformation. Hemorrhagic strokes can also arise from a hemorrhagic transformation of an ischemic stroke which weakens the blood vessels in the infarct, or a hemorrhage from primary or metastatic tumors in the CNS which contain abnormally weak blood vessels. Hemorrhagic stroke can also arise from iatrogenic causes such as direct surgical injury to a brain blood vessel. An aneurysm is a ballooning of a weakened region of a blood vessel. If left untreated, the aneurysm continues to weaken until it ruptures and bleeds into the brain. An arteriovenous malformation (AVM) is a cluster of abnormally formed blood vessels. A cavernous malformation is a venous abnormality that can cause a hemorrhage from weakened venous structures. Any one of these vessels can rupture, also causing bleeding into the brain. Hemorrhagic stroke can also result from physical trauma. Hemorrhagic stroke in one part of the brain can lead to ischemic stroke in another through shortage of blood lost in the hemorrhagic stroke.

One patient class amenable to treatments are patients undergoing a surgical procedure that involves or may involve a blood vessel supplying the brain, or otherwise on the brain or CNS. Some examples are patients undergoing cardiopulmonary bypass, carotid stenting, diagnostic angiography of the brain or coronary arteries of the aortic arch, vascular surgical procedures and neurosurgical procedures. Additional examples of such patients are discussed in section IV above. Patients with a brain aneurysm are particularly suitable. Such patients can be treated by a variety of surgical procedures including clipping the aneurysm to shut off blood, or performing endovascular surgery to block the aneurysm with small coils or introduce a stent into a blood vessel from which an aneurysm emerges, or inserting a microcatheter. Endovascular procedures are less invasive than clipping an aneurysm and are associated with a better patient outcome but the outcome still includes a high incidence of small infarctions. Such patients can be treated with an inhibitor of PSD95 interaction with NMDAR 2B and particularly the agents described above including the peptide YGRKKRRQRRRKLSSIESDV (SEQ ID NO:6, also known as Tat-NR2B9c). The timing of administration relative to performing surgery can be as described above for the clinical trial.

Another class of patients amenable to treatment are patients having a subarachnoid hemorrhage with or without an aneurysm (see U.S. 61/570,264).

IV. Effective Regimes of Administration

After reconstitution, a lyophilized formulation, is administered such that the active agent (e.g., NR2B9c) is administered in an amount, frequency and route of administration effective to cure, reduce or inhibit further deterioration of at least one sign or symptom of a disease in a patient having the disease being treated. A therapeutically effective amount means an amount of active agent sufficient significantly to cure, reduce or inhibit further deterioration of at least one sign or symptom of the disease or condition to be treated in a population of patients (or animal models) suffering from the disease treated with an agent of the invention relative to the damage in a control population of patients (or animal models) suffering from that disease or condition who are not treated with the agent. The amount is also considered therapeutically effective if an individual treated patient achieves an outcome more favorable than the mean outcome in a control population of comparable patients not treated by methods of the invention. A therapeutically effective regime involves the administration of a therapeutically effective dose at a frequency and route of administration needed to achieve the intended purpose.

For a patient suffering from stroke or other ischemic condition, the active agent is administered in a regime comprising an amount frequency and route of administration effective to reduce the damaging effects of stroke or other ischemic condition. When the condition requiring treatment is stroke, the outcome can be determined by infarction volume or disability index, and a dosage is considered therapeutically effective if an individual treated patient shows a disability of two or less on the Rankin scale and 75 or more on the Barthel scale, or if a population of treated patients shows a significantly improved (i.e., less disability) distribution of scores on a disability scale than a comparable untreated population, see Lees et at L, N Engl J Med 2006; 354:588-600. A single dose of agent is usually sufficient for treatment of stroke.

The invention also provides methods and formulations for the prophylaxis of a disorder in a subject at risk of that disorder. Usually such a subject has an increased likelihood of developing the disorder (e.g., a condition, illness, disorder or disease) relative to a control population. The control population for instance can comprise one or more individuals selected at random from the general population (e.g., matched by age, gender, race and/or ethnicity) who have not been diagnosed or have a family history of the disorder. A subject can be considered at risk for a disorder if a "risk factor" associated with that disorder is found to be associated with that subject. A risk factor can include any activity, trait, event or property associated with a given disorder, for example, through statistical or epidemiological studies on a population of subjects. A subject can thus be classified as being at risk for a disorder even if studies identifying the underlying risk factors did not include the subject specifically. For example, a subject undergoing heart surgery is at risk of transient cerebral ischemic attack because the frequency of transient cerebral ischemic attack is increased in a population of subjects who have undergone heart surgery as compared to a population of subjects who have not.

Other common risk factors for stroke include age, family history, gender, prior incidence of stroke, transient ischemic attack or heart attack, high blood pressure, smoking, diabetes, carotid or other artery disease, atrial fibrillation, other heart diseases such as heart disease, heart failure, dilated cardiomyopathy, heart valve disease and/or congenital heart defects; high blood cholesterol, and diets high in saturated fat, trans fat or cholesterol.

In prophylaxis, a lyophilized formulation after reconstitution is administered to a patient at risk of a disease but not yet having the disease in an amount, frequency and route sufficient to prevent, delay or inhibit development of at least one sign or symptom of the disease. A prophylactically effective amount means an amount of agent sufficient significantly to prevent, inhibit or delay at least one sign or symptom of the disease in a population of patients (or animal models) at risk of the disease relative treated with the agent compared to a control population of patients (or animal models) at risk of the disease not treated with a chimeric agent of the invention. The amount is also considered prophylactically effective if an individual treated patient achieves an outcome more favorable than the mean outcome in a control population of comparable patients not treated by methods of the invention. A prophylactically effective regime involves the administration of a prophylactically effective dose at a frequency and route of administration needed to achieve the intended purpose. For prophylaxis of stroke in a patient at imminent risk of stroke (e.g., a patient undergoing heart surgery), a single dose of agent is usually sufficient.

Depending on the agent, administration can be parenteral, intravenous, nasal, oral, subcutaneous, intra-arterial, intracranial, intrathecal, intraperitoneal, topical, intranasal or intramuscular. Intravenous administration is preferred for peptide agents.

For administration to humans, a preferred dose of active agent (e.g., Tat-NR2B9c) is 2-3 mg/kg and more preferably 2.6 mg/kg. Indicated dosages should be understood as including the margin of error inherent in the accuracy with which dosages can be measured in a typical hospital setting. Such amounts are for single dose administration, i.e., one dose per episode of disease.

Active agents, such as Tat-NR2B9c are preferably delivered by infusion into a blood vessel, more preferably by intravenous infusion. The time of the infusion can affect both side effects (due e.g., to mast cell degranulation and histamine release) and efficacy. In general, for a given dosage level, a shorter infusion time is more likely to lead to histamine release. However, a shorter infusion time also may result in improved efficacy. Although practice of the invention is not dependent on an understanding of mechanism, the latter result can be explained both because of the delay being significant relative to development of pathology in the patient and because of the delay being significant relative to the plasma half-life of the chimeric agent, as a result of which the chimeric agent does not reach an optimal therapeutic level. For the chimeric agent Tat-NR2B9c, a preferred infusion time providing a balance between these considerations is 5-15 minutes and more preferably 10 min. Indicated times should be understood as including a marking of error of +/−10%. Infusion times do not include any extra time for a wash out diffusion to wash out any remaining droplets from an initial diffusion that has otherwise proceeded to completion. The infusion times for Tat-NR2B9c can also serve as a guide for other active agents.

Although the invention has been described in detail for purposes of clarity of understanding, certain modifications may be practiced within the scope of the appended claims. All publications, accession numbers, and patent documents cited in this application are hereby incorporated by reference in their entirety for all purposes to the same extent as if each were so individually denoted. To the extent more than one sequence is associated with an accession number at different times, the sequences associated with the accession number as of the effective filing date of this application is meant. The effective filing date is the date of the earliest priority application disclosing the accession number in question. Unless otherwise apparent from the context any element, embodiment, step, feature or aspect of the invention can be performed in combination with any other.

EXAMPLES

Examples 1-7 show that an acetate salt of TAT-NR2B9c can be formulated in lyophilized form with histidine and trehalose. Example 9 shows that the chloride salt of TAT-NR2B9c offers significantly greater stability than the acetate salt in an otherwise identical lyophilized formulation. Example 8 shows that the chloride salt of TAT-NR2B9c formulated in histidine and trehalose also gives improved stability relative to a previously described lyophilized formulation of TAT-NR2B9c from normal saline.

Example 1: Demonstration that Standard Buffers and Excipients do not Interfere with the Efficacy of TAT-NR2B9c In Vivo Five liquid toxicology formulations were compounded targeted at a 20 mg/mL concentration of TAT-NR2B9c. Table 1 includes the vehicle composition, Lot Number, and the potency, purity and pH at the time of compounding. Approximately 5 mL of each formulation was vialed for testing. Vials were frozen at −20 to simulate transport or liquid storage conditions.

TABLE 1 composition of TAT-NR2B9c formulations for efficacy testing in vivo

| Formulation | Vehicle Composition | PTek Lot # | Potency[1] (mg/mL) | Purity (% Area of NA-1 peak) | pH[3] |
|---|---|---|---|---|---|
| 1 | 50 mM sodium phosphate, 76.9 mM NaCl, pH 7.0 | 1205-1-17-1 | 20.5 | 97.87 | 6.7 |
| 2 | 50 mM sodium phosphate, 154 mM Mannitol, pH 7.0 | 1205-1-17-2 | 20.0 | 96.34[2] | 6.5 |
| 3 | 50 mM histidine, 154 mM Mannitol, pH 6.5 | 1205-1-17-3 | 19.9 | 98.38 | 6.4 |
| 4 | 50 mM histidine, 154 mM Trehalose, pH 6.5 | 1205-1-17-4 | 20.8 | 99.16 | 6.4 |
| 5 | 50 mM histidine, 5% Dextran-40, pH 6.5 | 1205-1-18-1 | 19.4 | 98.81 | 6.4 |

[1]Potency and purity were evaluated by RP-HPLC analysis using a TFA method
[2]The purity of formulation #2 is notably lower than the other formulations.
[3]The pH of the phosphate buffered formulations noticeably deviated from the initial buffer pH of 7.0.

It was noted that phosphate buffered formulation did not maintain pH as well as the histidine buffers did between formulation and testing, indicating that histidine may be a superior buffer for formulation.

Formulations 1-5 were tested in the 3-PIAL Vessel Occlusions (3PVO) model of stroke in rats. Rats subjected to stroke were given one of the formulations by intravenous administration into the femoral vein, and then the animals were sacrificed 24 hours after the stroke. Brains were harvested, fixed and stained with triphenyltetrazolium chloride (TTC) to visualize the ischemic portions of the brain. All of the formulations tested were able to provide significant neuroprotection in animals relative to the saline-only control (FIG. 1).

Methods

Three Pial Vessel Occlusion Model of Ischemia

Experiments were performed on rats. For permanent three pial vessels occlusion (3PVO) was performed as described previously [Angiogenic protection from focal ischemia with angiotensin II type 1 receptor blockade in the rat. Forder et al., Am J Physiol Heart Circ Physiol. 2005 April; 288(4): H1989-96]. In brief, 250 g to 350 g rats were anesthetized with a 0.5 ml/kg intramuscular injection of ketamine (100 mg/kg), acepromazine (2 mg/kg), and xylazine (5 mg/kg), supplemented with one-third of the initial dose as required.

An anal temperature probe was inserted, and the animal was placed on a heating pad maintained at about 37° C. The skull was exposed via a midline incision and scraped free of tissue. Using a dissecting microscope and a pneumatic dental drill, a 6- to 8-mm cranial window was made over the right somatosensory cortex (2 mm caudal and 5 mm lateral to bregma) by drilling a rectangle through the skull and lifting off the piece of skull while keeping the dura intact. The 3 pial arteriolar middle cerebral artery branches were cauterized around the barrel cortex were selected and electrically cauterized through the dura. After the cauterizations, the scalp was sutured. Each rat was returned to its individual cage under a heating lamp to maintain body temperature until the rat fully recovered. Food and water was supplied. One hour after 3PVO ischemia the rats were injected with NA1 formulations at 3 nmol/g in ~0.45 mL saline based upon rat weight. Doses were administered over 5 minutes.

Twenty-four hours after surgery, the brain was quickly harvested. Coronal slices (2 mm) were taken through the brain and incubated in 2% triphenyltetrazolium chloride (TTC) (Sigma-Aldrich St. Louis Mo.) for 15 min at 37° C. Images were scanned (CanoScan 4200F Canon) and quantitated.

Example 2: Determination of TAT-NR2B9c Stability in Different Buffers and at Different pH Values Screening of Buffers Ten buffers were compounded at 1 mg/mL TAT-NR2B9c for excipient screening. Samples were stored at 25° C./60% relative humidity (RH) and 40° C./75% RH. Samples were tested for stability (purity) at t=0 and t=1 week for purity by RP-HPLC (TFA and MSA methods), and the results are shown in Tables 2 and 3.

Results indicate improved stability for TAT-NR2B9c in liquid media buffered between pH 6.0 and pH 6.5. Degradation appears to increase outside of this range in either direction. Data generated with the MSA method showed clear degradation patterns that were both pH and buffering species dependent, and provided valuable insight into future formulation development. Results for main peak purity by % HPLC Area using the MSA method are provided in Table 2, while results for main peak purity by % HPLC Area using the TFA method are provided in Table 3.

TABLE 2

% Area of the Main Peak by MSA Method, TAT-NR2B9c

| Sample | t = 0 | t = 1 week 25° C. | t = 1 week 40° C. |
|---|---|---|---|
| His, 6.0 | 98.5 | 98.5 | 98.0 |
| His, 6.5 | 98.5 | 98.6 | 97.3 |
| His, 7.0 | 98.5 | 98.4 | 97.0 |
| Phos, 6.0 | 98.5 | 98.2 | 97.0 |
| Phos, 6.5 | 98.5 | 97.9 | 97.3 |
| Phos, 7.0 | 98.5 | 97.9 | 96.0 |
| Phos, 7.5 | 98.5 | 97.6 | 95.2 |
| Citr, 5.5 | 98.5 | 98.3 | 94.4 |
| Citr, 6.0 | 98.5 | 98.4 | 97.4 |
| Citr, 6.5 | 98.5 | 98.7 | 97.7 |

TABLE 3

% Area of the Main Peak by TFA Method, TAT-NR2B9c

| Sample | t = 0 | t = 1 week 25° C. | t = 1 week 40° C. |
|---|---|---|---|
| His, pH 6.0 | 99.5 | 98.8 | 99.2 |
| His, pH 6.5 | 99.5 | 98.4 | 99.4 |
| His, pH 7.0 | 99.5 | 98.3 | 96.7 |
| Phos, 6.0 | 99.5 | 99.8 | 97.9 |
| Phos, 6.5 | 99.5 | 99.5 | 98.6 |
| Phos, 7.0 | 99.5 | 98.6 | 98.3 |
| Phos, 7.5 | 99.5 | 98.0 | 93.2 |
| Citr, 5.5 | 99.5 | 98.0 | 95.1 |
| Citr, 6.0 | 99.5 | 99.0 | 98.2 |
| Citr, 6.5 | 99.5 | 99.5 | 99.1 |

Results indicate that TAT-NR2B9c solution stability is best maintained in pH 6.0 to 6.5 buffered media and the vehicle is still well tolerated for administration by IV. In general, histidine and citrate buffering systems were able to maintain TAT-NR2B9c in an intact form even when kept at accelerated stability conditions of 25° C. or 40° C. for 1 week.

There are several factors to consider when selecting a buffering species: the specific degradation patterns that occur in each media, and any data on identified related substances or toxicology concerns may streamline the decision process if specified related substances should be avoided. For the period tested, histidine and citrate buffers between pH 6 and 6.5 showed few degradation products. The histidine buffer itself used in this study contained a contaminant that was present in the histidine buffer in the absence of added TAT-NR2B9c. Therefore, identification of a supplier of histidine without such a contaminant would make analysis simpler. Table 4 provides a summary of the buffer species from the standpoint of TAT-NR2B9c stability.

TABLE 4

Buffering Species Selection

| Species | pH | Pro | Con |
|---|---|---|---|
| Histidine | 6.0 | Excellent stability, historic use in lyophilization applications, well within buffering range | Chromatographic interference, but chromatography could possibly be improved by new histidine vendor |
| Citrate | 6.0 | Improved stability, historic use in lyophilization applications, well within buffering range | |
| Histidine | 6.5 | Improved stability, historic use in lyophilization applications, well within buffering range | Chromatographic interference, but chromatography could possibly be improved by new histidine vendor |
| Citrate | 6.5 | Excellent stability, historic use in lyophilization applications, well within buffering range | Target pH of 6.5 may be on the edge of the ideal buffering range for the citrate species |

TABLE 4-continued

Buffering Species Selection

| Species | pH | Pro | Con |
|---|---|---|---|
| Phosphate | 6.5 | Improved stability, historic use of phosphate species in NA-1 formulations | Phosphate species has been historically avoided for lyophilization formulations |

Example 3: Determination of TAT-NR2B9c Stability in Histidine and Citrate Buffers and at Different pH Values with Varying Amounts of Sodium Chloride The goal of this study was to demonstrate the effects of sodium chloride (NaCl) on pH and TAT-NR2B9c stability in liquid formulations. Buffer formulations with 1 mg/mL TAT-NR2B9c are listed in Table 5, and results for pH are provided in Table 6. The data show fairly consistent results for the duration of the study. However, notable shifts occurred in citrate with the addition of NaCl, where the buffering capacity was impacted and the pH dropped by ~0.2 units. Selected pH's of 6.0 and 6.5 are on the outside edge of citrate's ideal buffering range (pH 2.5-5.6), so this may cause difficulties with various additives during the compounding process and should be considered when evaluating formulation robustness.

TABLE 5

Buffer formulations for examining the effect of salt on pH

| Vehicle # | Buffer | Target pH | NaCl |
|---|---|---|---|
| 1 | 50 mM Citrate | 6.0 | NA |
| 2 | 50 mM Citrate | 6.0 | 200 mM |
| 3 | 50 mM Citrate | 6.5 | NA |
| 4 | 50 mM Citrate | 6.5 | 200 mM |
| 5 | 50 mM Histidine | 6.0 | NA |
| 6 | 50 mM Histidine | 6.0 | 200 mM |
| 7 | 50 mM Histidine | 6.5 | NA |
| 8 | 50 mM Histidine | 6.5 | 200 mM |

TABLE 6 pH Stability of TAT-NR2B9c formulations in under frozen and accelerated temperature conditions

| Vehicle # | Buffer | Target pH | Measured pH t = 0 Vehicle | Measured pH t = 0 Vehicle + NA-1 | Measured pH t = 1 week Vehicle + NA-1 −20° C. | Measured pH t = 1 week Vehicle + NA-1 40° C./ 75% RH |
|---|---|---|---|---|---|---|
| 1 | Citr | 6.0 | 6.1 | 6.0 | 6.1 | 6.0 |
| 2 | | 6.5 | 6.6 | 6.5 | 6.6 | 6.6 |
| 3 | His | 6.0 | 6.0 | 5.9 | 6.2 | 6.0 |
| 4 | | 6.5 | 6.5 | 6.5 | 6.6 | 6.7 |
| 5 | Citr + NaCl | 6.0 | 5.8 | 5.8 | 5.9 | 5.8 |
| 6 | | 6.5 | 6.3 | 6.2 | 6.3 | 6.3 |
| 7 | His + NaCl | 6.0 | 6.1 | 6.0 | 6.2 | 6.0 |
| 8 | | 6.5 | 6.6 | 6.6 | 6.7 | 6.7 |

The results indicate that the addition of 200 mM NaCl to the histidine and citrate buffered TAT-NR2B9c solutions does not significantly affect the pH of the solutions whether stored for a week frozen or at the accelerated temperature of 40° C.

Next, we examined the stability of TAT-NR2B9c in these formulations when stored 1 week at frozen and accelerated temperatures. Table 7 shows the results of the testing using the RP-HPLC method with an MSA gradient. The data is also presented in FIGS. 2A and 2B. FIG. 2A presents the accelerated stability of formulations sorted from left to right (low to high stability). FIG. 2B shows the relative accelerated stability by buffering agent.

TABLE 7

Purity (MSA Method), TAT-NR2B9c

| Vehicle | pH 6.0 | | pH 6.5 | |
|---|---|---|---|---|
| | −20° C. | 40° C. | −20° C. | 40° C. |
| His | 98.1 | 92.8 | 98.5 | 96.9 |
| His + NaCl | 98.4 | 95.0 | 98.4 | 97.7 |
| Citr | 97.5 | 96.0 | 99.0 | 97.5 |
| Citr + NaCl | 98.4 | 96.7 | 98.7 | 98.4 |

These results indicate that TAT-NR2B9c solution stability is best maintained at pH 6.5, and the addition of NaCl may offer a slight improvement in stability (FIGS. 2A and 2B). Due to improved buffering capacity and comparable stability of the histidine buffer, especially when the contaminant migrating with a relative retention time (RRT) of 0.28 is excluded (contaminant area included in the table above, resulting in a lower stability value for the TAT-NR2B9c peak area), the histidine buffering species at pH 6.5 is the best formulation to move into lyophilization studies.

Vehicles at pH 6.5 are well tolerated for administration by IV.

Example 4: Selection of Bulking Agents for TAT-NR2B9c to Form a Stable Lyophilized Cake To identify bulking agents that would generate a nice cake upon lyophilization and improve stability, we compounded several 20 mg/mL TAT-NR2B9c solutions in 50 mM histidine buffer, bulking agent and NaCl as outlined in Table 8. To simulate the time and handling temperatures that TAT-NR2B9c formulations may be exposed to during the lyophilization process, these samples were stored at −20° C. (control) and 40° C./75% RH (test), and were analyzed after one week of storage for purity by HPLC (MSA method) and pH. Results are for pH stability are outlined in Table 9, and results for the stability of TAT-NR2B9c in the different liquid formulations are shown in Table 10 and FIG. 3.

TABLE 8

Bulking Agent Sample Matrix

| Vehicle # | Buffer | Bulking Agent | NaCl |
|---|---|---|---|
| 1 | 50 mM histidine, pH 6.5 | 120 mM Mannitol | |
| 2 | 50 mM histidine, pH 6.5 | 120 mM Mannitol | 75 mM |
| 3 | 50 mM histidine, pH 6.5 | 120 mM Trehalose | |
| 4 | 50 mM histidine, pH 6.5 | 120 mM Trehalose | 75 mM |
| 5 | 50 mM histidine, pH 6.5 | 5% Dextran-40 | |
| 6 | 50 mM histidine, pH 6.5 | 5% Dextran-40 | 75 mM |

TABLE 9 pH, Bulking Agent Samples

| Vehicle | Target pH | pH, −20° C. | pH, 40° C. |
|---|---|---|---|
| Mannitol | 6.5 | 6.5 | 6.5 |
| Mannitol + NaCl | 6.5 | 6.5 | 6.5 |
| Trehalose | 6.5 | 6.5 | 6.4 |
| Trehalose + NaCl | 6.5 | 6.5 | 6.4 |
| Dextran-40 | 6.5 | 6.5 | 6.3 |
| Dextran-40 + NaCl | 6.5 | 6.5 | 6.4 |

TABLE 10

Purity by % Area of TAT-NR2B9c Peak, MSA Method

| | | % Area of NA-1 Peak | |
|---|---|---|---|
| Vehicle # | Vehicle | −20 C. | 40 C. |
| 1 | Mannitol | 99.2 | 98.5 |
| 2 | Mannitol + NaCl | 99.4 | 98.6 |
| 3 | Trehalose | 99.1 | 98.5 |
| 4 | Trehalose + NaCl | 99.3 | 98.3 |
| 5 | Dextran-40 | 99.2 | 97.6 |
| 6 | Dextran-40 + NaCl | 99.0 | 97.7 |

Results of Bulking Agent Liquid Formulations on TAT-NR2B9c Stability

Mannitol, Trehalose and Dextran-40 maintain the pH at 6.5 well (Table 9) and there is approximately a 1% decrease in purity (Table 10) over 1 week as a liquid formation when stored at high temperature. In terms of the chemical stability of the TAT-NR2B9c lyophilization fill solution, mannitol and trehalose are preferred bulking agents as they confer better stability to TAT-NR2B9c than the dextran-40 solutions (FIG. 3).

Example 5: Thermal Analysis of Bulking Agents to Facilitate Design of Lyophilization Cycles As part of the lyophilization cycle development for TAT-NR2B9c lyophilized drug product, proposed fill solutions from the bulking agent sample matrix (Table 8) were evaluated by Differential Scanning calorimetry (DSC) for thermal characteristics including glass transition (Tg) in the formulation. Results are listed in Table 11 and DSC traces are included in FIGS. 4A-6B.

TABLE 11

Glass Transitions of TAT-NR2B9c Lyophilization Fill Solutions

| Vehicle | $T_g$ |
|---|---|
| 50 mM histidine, pH 6.5, 120 mM Mannitol | −37.25° C. |
| 50 mM histidine, pH 6.5, 120 mM Mannitol, 75 mM NaCl | −42.51° C. |
| 50 mM histidine, pH 6.5, 120 mM Trehalose | −28.25° C. |
| 50 mM histidine, pH 6.5, 120 mM Trehalose, 75 mM NaCl | −35.74° C. |
| 50 mM histidine, pH 6.5, 5% Dextran-40 | −17.09° C. |
| 50 mM histidine, pH 6.5, 5% Dextran-40, 75 mM NaCl | −22.49° C. |

At a TAT-NR2B9c concentration of 20 mg/mL, tested TAT-NR2B9c formulations showed a thermal profile characterized by a broad melting event with onset at a low temperature. This extended melt masked the crystallization event typically seen in mannitol formulations, and may indicate that a robust freeze drying cycle must be performed where the product never exceeds the glass transition temperature. In this case, based on the observed glass transitions of the TAT-NR2B9c drug product fill solution, the use of mannitol as a bulking agent would require a primary drying temperature lower than −40° C., the typical limit of feasibility for a scalable cycle. In terms of thermal profiles, Trehalose and Dextran-40 are superior for use as a bulking agent. However, given that the stability of TAT-NR2B9c in the liquid formulations containing trehalose was superior to those containing Dextran, trehalose would be the preferred bulking agent of those tested.

Due to the relatively low Tg temperatures that would likely require a longer lyophilization cycle to dry, we looked at a wider range of standard bulking agents and looked to reduce the fill volume into the container closure system so that there would be a reduced volume of liquid to lyophilize. In an effort to decrease the fill volume and maintain 270 mg/vial, a solubility study of TAT-NR2B9c in Histidine, pH 6.5 and in Histidine+Trehalose, pH 6.5 was performed. Samples were visually analyzed at 35, 50, 75 and 100 mg/mL. All solutions were clear at t=0 and t=24 hours. Based on this data, we could use fill volume lower than 3 mL, which using a 90 mg/mL TAT-NR2B9c formulation would give provide 270 mg in a target vial. A wide range of quantities may be required in a vial, but 270 mg would provide a 2.6 mg/kg dose for a 100 kg patient. Assuming the target reconstitution concentration for patient administration is still 20 mg/mL (but can be from 1 mg/ml to 100 mg/ml), then a 20-mL lyophilization vial containing 270 mg of TAT-NR2B9c can be used with a reconstitution volume of 13.5 mL. Therefore, optimal volumes of liquid for lyophilization of TAT-NR2B9c in the vial would be between 2.5 mL and 10 mL.

A wider range of bulking agents were tested prior to advancing into lyophilization development, and the Tg's are shown in Table 12. The 100 mg/mL TAT-NR2B9c in histidine, pH 6.5 was also evaluated by DSC and the data is included in Table 12.

TABLE 12

DSC Data, Formulations

| | | Vehicle | | |
|---|---|---|---|---|
| Formulation | Bulking Agent | $T_g$ | Temp of Crystallization | DP Fill Solution $T_g$ |
| 1 | Sorbitol | −41.03° C. | | |
| 2 | Dextrose | −38.78° C. | | |
| 3 | Sucrose | −31.09° C. | | |
| 4 | Mannitol | −37.38° C. | −22.91° C. | −35.49° C. |
| 5 | Trehalose | −29.93° C. | | −28.25° C. |
| 6 | Lactose | −27.93° C. | | |
| 7 | 75:25 Trehalose:Dextran-40 | −25.07° C. | | −25.07° C. |
| 8 | 50:50 Trehalose:Dextran-40 | −22.60° C. | | −22.60° C. |
| 9 | 25:75 Trehalose:Dextran-40 | −18.55° C. | | −18.55° C. |
| 10 | Dextran-40 | | | −17.09° C. |
| 11 | 100 mg/mL NA-1 in Histidine, pH 6.5 | | | −21.67° C. |

Based on the DSC data in Table 12, there are several formulation options for both active and placebo drug products. In general, formulations 5 and 11 are the most promising for the active product with respect to the Tg. Any bulking agent may be suitable for use in a placebo product, but Formulation 4 (Mannitol) will have the shortest cycle length if annealed, and may be the most desirable should the appearance match the active.

As we determine an optimal active formulation, it is important to consider solution stability, lyophilization cycle robustness, and chemical stability. Formulation 5 from Table 12 (Trehalose) demonstrated good solution stability and lyophile chemical stability at accelerated conditions (data shown subsequently), but requires a longer lyophilization cycle at a fill configuration of 13.5 mL. This longer cycle length may not be ideal for commercial manufacture in the future, where a shorter cycle is desirable. Formulation 11 from Table 12 (without a bulking agent, at 100 mg/mL TAT-NR2B9c) has a higher glass transition temperature than Formulation 5, allowing for a warmer, shorter cycle. In addition, a decreased fill volume will significantly shorten the run time as there will be less ice to sublimate from each vial.

Example 6: Stability of TAT-NR2B9c with Varying Bulking Agents, Scales and Lyophilization Conditions Bulking Agent Accelerated Stability A small batch of TAT-NR2B9c drug product was lyophilized to evaluate solid state stability after 1 week at 25° C., 40° C., and 60° C. TAT-NR2B9c was compounded at an active concentration of 20 mg/mL in three different vehicles. Samples were evaluated for appearance, reconstitution, pH, amount and purity by HPLC (MSA method) at t=0 and t=1 week. Water content was evaluated at t=0 only.

All TAT-NR2B9c drug products appeared as white, lyophilized cakes and reconstituted in less than 10 seconds at t=0 and t=1 week.

The drug product vehicles are described in Table 13 and are listed with the respective glass transition temperature and water content results. The pH, TAT-NR2B9c amount and TAT-NR2B9c purity results are described in Tables 14-16.

TABLE 13

Bulking Agent Sample Matrix: Tg, and % Water Content

| Vehicle # | Vehicle | $T_g$ | t = 0 % Water Content |
|---|---|---|---|
| 1 | 50 mM His, pH 6.5 + 120 mM Trehalose | −29.93° C. −28.25° C. w/NA-1 | 0.29% |
| 2 | 50 mM His, pH 6.5 + 5% Dextran-40 | −22.60° C. | 0.05% |
| 3 | 50 mM His, pH 6.5 + 1:1 120 mM Trehalose: 5% Dextran-40 | −17.09° C. w/NA-1 | 0.10% |

TABLE 14 pH, Bulking Agent Lyo Small Scale #1

| | | Measured pH | | | |
|---|---|---|---|---|---|
| Bulking Agent | Theoretical pH | t = 0 | t = 1 wk 25° C. | t = 1 wk 40° C. | t = 1 wk 60° C. |
| Trehalose | 6.5 | 6.4 | 6.4 | 6.4 | 6.4 |
| Dextran-40 | 6.5 | 6.4 | 6.3 | 6.3 | 6.3 |
| 1:1 Trehalose:Dextran | 6.5 | 6.4 | 6.3 | 6.4 | 6.4 |

TABLE 15

Amount (mg/vial), Bulking Agent Lyo Small Scale #1

| Bulking Agent | t = 0 | t = 1 week 25° C. | t = 1 week 40° C. | t = 1 week 60° C. |
|---|---|---|---|---|
| Trehalose | 20.6 | 20.3 | 20.7 | 20.7 |
| Dextran-40 | 19.4 | 19.8 | 19.5 | 19.1 |
| 1:1 Trehalose:Dextran-40 | 20.3 | 20.8 | 20.2 | 20.2 |

TABLE 16

Purity (% Area by HPLC), Bulking Agent Lyo Small Scale #1

| Bulking Agent | t = 0 | t = 1 week 25° C. | t = 1 week 40° C. | t = 1 week 60° C. |
|---|---|---|---|---|
| Trehalose | 98.8 | 98.8 | 98.8 | 98.4 |
| Dextran-40 | 98.9 | 98.9 | 98.6 | 96.5 |
| 1:1 Trehalose:Dextran-40 | 98.9 | 98.8 | 98.6 | 97.5 |

All three bulking agents, Trehalose, Dextran-40 and Trehalose:Dextran-40, maintain the pH at 6.5 (Table 14) and there is a range of 0.5-2.5% decrease in purity at 60° C. after 1 week (Table 15). Both drug products containing dextran-40 and stored at 60° C. showed growth in related substances at a retention time (RT) ~6.0. These related substances were not present in the trehalose samples, suggesting that trehalose has a stabilizing effect in the lyophilized drug product and dextran-40 can cause a specific degradation product.

The inclusion of dextran-40 in the bulking agent allows for a warmer primary drying temperature, but dextran-40 as a bulking agent demonstrated the poorest stability. The combination of trehalose and dextran-40 (1:1) results in a glass transition temperature that is approximately 10° C. warmer than trehalose alone. However, it appears that the 60° C. stability is intermediate to the trehalose and dextran alone samples, so that trehalose is a preferred bulking agent.

Lyophilized TAT-NR2B9c Formulation Development: Small Scale Experiment #2

A small batch of TAT-NR2B9c drug product was lyophilized to evaluate setting the shelf temperature at 5° C. during primary drying. TAT-NR2B9c was compounded at an active concentration of 27 mg/mL in 50 mM Histidine, pH 6.5 and 120 mM Trehalose. The cycle parameters are outlined in Table 17. Four 20-mL glass lyophilization vials were filled with 10 mL. Two vials were probed with temperature probes.

TABLE 17

Small Scale 2, TAT-NR2B9c Formulation Development

| Function | Temperature (° C.) | Hold/ Rate | Rate (° C./ minute) | Time (minutes) | Pressure (mTorr) |
|---|---|---|---|---|---|
| Load | 5 | Hold | — | 0 | Ambient |
| Equilibration | 5 | Hold | — | 120 | Ambient |
| Freeze | −40 | Rate | 0.5 | 90 | Ambient |
| Freeze | −40 | Hold | — | 240 | Ambient |
| Primary Drying[1] | 5 | Rate | 0.25 | 180 | 225 |
| Primary Drying[1] | 5 | Hold | — | 2050 | 50 |
| Secondary Drying | 25 | Rate | 0.1 | 200 | 50 |
| Secondary Drying | 25 | Hold | — | 1440 | 50 |
| Stopper | 20 | Hold | — | — | Nitrogen/ Ambient |
| Unload | 20 | Hold | — | — | Ambient |

[1]Primary drying temperature based on large vial size and fill volume, not directly related to glass transition temperature.

Due to the large fill volume, it is necessary to set the shelf temperature considerably warmer than the glass transition temperature in order to compensate for evaporative cooling. The solution temperature during primary drying was at −29° C., which is near the glass transition temperature of −28° C. from the DSC thermal analysis.

90 mg/mL TAT-NR2B9c Lyophile Accelerated Stability (Small Scale 3)

Prior to compounding the small scale 3 fill solution, a 90 mg/mL TAT-NR2B9c in buffer (50 mM Histidine, pH 6.5) was evaluated for pH. The pH of the solution was 6.04. It was determined that with the increased concentration of TAT-NR2B9c, the buffering strength also needed to increase. Solutions were prepared at 150 mM, 100 mM, 75 mM, and water and evaluated for pH. The pHs are listed in Table 18. Small scale 3 was compounded in a 100 mM Histidine buffer at pH 6.5, and the pH was re-adjusted to 6.5 after addition of TAT-NR2B9c.

TABLE 18 pH, 90 mg/mL TAT-NR2B9c in Histidine Buffers, pH 6.5

| Buffer | pH |
| --- | --- |
| Water | 6.04 |
| 50 mM | 6.04 |
| 75 mM | 6.29 |
| 100 mM | 6.29 |
| 150 mM | 6.14 |

A small batch of TAT-NR2B9c drug product was lyophilized to evaluate solid state stability after 1 week storage at 25° C. and 60° C. Two 90 mg/mL TAT-NR2B9c formulations were compounded (buffer and buffer with trehalose). Samples were evaluated for appearance, reconstitution, water content and purity by HPLC (MSA method) at t=0 and t=1 week.

All TAT-NR2B9c drug products appeared as white, lyophilized cakes. Some cakes were cracked. Placebo formulations were visually similar to the active formulations.

Reconstitution time was approximately 1.5 minutes compared to less than 10 seconds in the previous formulations. The increased reconstitution time is most likely due to the increased concentrations of TAT-NR2B9c and histidine. Further tests showed good stability of TAT-NR2B9c with histidine buffer concentrations of 50 and 75 mM, with shortened resuspension times. Also, due to the 2-mL vial size used for this study, only 1 mL of water was added to the lyophile. The actual reconstitution volume is 4.5 mL in this small scale configuration. The reconstitution time will most likely improve when a larger volume of diluent is used.

Vials were placed on stability at 25° C. and 60° C. and tested after 1 week of storage.

Based on the visual appearance data, the trehalose sample gave a more elegant cake. The lyophilization cycle was run conservatively over 5 days, with a primary drying temperature of −32°. Based on the temperature probe data, the cycle can be shortened, demonstrating that with the higher concentration and lower fill volume the optimized cycle will be shorter.

Purity results are outlined in Table 19.

TABLE 19

| Formulation | Composition | Fill Solution | t = 0 | t = 1 week, 25° C./ 60% RH | t = 1 week, 60° C. |
| --- | --- | --- | --- | --- | --- |
| 1 | 100 mM His, pH 6.5 | 99.2 | 99.3 | 99.3 | 97.8 |
| 2 | 100 mM His, pH 6.5 + 120 mM Trehalose | 99.2 | 99.3 | 99.2 | 98.7 |

Based on this accelerated stability data, trehalose demonstrates a stabilizing effect on the TAT-NR2B9c formulation which improves the chemical stability of the lyophile. It is surprising that trehalose is able to confer this stabilizing effect while other standard bulking agents such as dextran and mannitol used for other peptides do not.

The reduced fill volume minimizes the competing evaporative cooling of the surrounding vials and minimizes the resistance to the sublimating water.

Lyophilization Cycle Development—Small Scale 4 (Placebo and Active)

Small scale 4 of the lyophilization cycle development was initiated to test the cake appearance and lyophilization conditions for a 3 mL fill. Samples tested were 100 mM His, pH 6.5 with 120 mM Trehalose and 90 mg/kg TAT-NR2B9c or an identical sample removing the Trehalose. A conservative, 4 day cycle was ran as described in Table 20. Placebo and active vials were included with a fill configuration of 3 mL into a 20-mL glass lyophilization vial instead of the small vials used for the previous experiments. An active temperature probe was used to confirm temperature during the lyophilization cycle. The resulting active vials is shown in FIG. 7A.

TABLE 20

Lyophilization Parameters for Small Scale 4

| Function | Temperature (° C.) | Hold/ Rate | Rate (° C./ minute) | Time (minutes) | Pressure (mTorr) |
| --- | --- | --- | --- | --- | --- |
| Load | 5 | Hold | — | 0 | Ambient |
| Equilibration | 5 | Hold | — | 120 | Ambient |
| Freeze | −40 | Rate | 0.5 | 90 | Ambient |
| Freeze | −40 | Hold | — | 120 | Ambient |
| Primary Drying | −30 | Rate | 0.25 | 40 | 225 |
| Primary Drying | −30 | Hold | — | 3400 | 50 |
| Secondary Drying | 25 | Rate | 0.1 | 550 | 50 |
| Secondary Drying | 25 | Hold | — | 1440 | 50 |
| Stopper | 20 | Hold | — | — | Nitrogen/ Ambient |
| Unload | 20 | Hold | — | — | Ambient |

Formulation at 90 mg/ml in a 20 mL vial formed an elegant cake on a 4 day cycle, and temperature probe data suggested that the cycle could be shortened to 3 days.

Water content for the placebo and active was 0.01% and 0.00%.

Lyophilization Cycle Development—Small Scale 5 (Placebo and Active)

Small Scale 5 was performed to look at developing a matching placebo vial for clinical trials and to look at resuspension times for formulations at a potential commercial scale (270 mg/vial). 10 placebo formulations and 1 active formulation were evaluated for appearance and reconstitution time. The active cakes were elegant, white cakes with minor shrinkage resulting in a crack around the surface of the vial wall. The placebo cakes were white with more cracks in cakes containing increasing amounts of trehalose.

Vials were reconstituted with 13.5 mL of water. The time to dissolve is listed in Table 21. The active lyophile resuspended immediately, but was cloudy for 17.6 sec before becoming a clear, colorless solution. All placebos were a clear, colorless solution.

TABLE 21

Reconstitution of Placebo and Active (SS5)

| Placebo Formulation # | Formulations Trehalose, mM | Histidine, mM | Total, mg/vial | Reconstitution Time (min) Vial #1 | Vial #2 |
|---|---|---|---|---|---|
| 1 (Control) | 120 | 100 | 170 | <10 sec | <10 sec |
| 2 | 200 | 100 | 252 | <10 sec | <10 sec |
| 3 | 300 | 100 | 355 | <10 sec | <10 sec |
| 4 | 400 | 100 | 457 | <10 sec | <10 sec |
| 5 | 500 | 100 | 560 | <10 sec | <10 sec |
| 6 | 120 | 20 | 133 | <10 sec | <10 sec |
| 7 | 200 | 20 | 215 | <10 sec | <10 sec |
| 8 | 300 | 20 | 317 | <10 sec | <10 sec |
| 9 | 400 | 20 | 420 | <10 sec | <10 sec |
| 10 | 500 | 20 | 523 | <10 sec | <10 sec |
| Active Formulation # | Trehalose, mM | Histidine, mM | NA-1, mg | Vial #1 | Vial #2 |
| 1 (Control) | 120 | 100 | 90 | 17.6 sec | NA |

Based on the stability, resuspension times, and lyophilization times, a preferred commercial formulation for TAT-NR2B9c, prelyophilization, would be 20-100 mM Histidine, 120 mM Trehalose pH 6.5. Trehalose concentrations can be increased without a loss of stability or cake elegance but resuspension times.

Examination of Increased Trehalose in Cake Formation and Placebo Matching by Visual Appearance and Resuspension Time.

To better match a placebo, varying concentrations of Trehalose were tested with and without TAT-NR2B9c, and at either 3 or 5 mL fill volumes.

First, the active formulations and the placebo formulations will be summarized. Then the lead visual matches for the 3-mL fill and the 5-mL fill will be highlighted. Analytical samples (fill solution and one potency sample) are currently being analyzed. Tables 22 and 23 show a subset of the formulations tested.

TABLE 22

Active Formulations

| Formulation | Fill Volume | Composition |
|---|---|---|
| 1 | 3-mL | 270 mg/vial in 120 mM Trehalose + 100 mM Histidine, pH 6.5 |
| 2 | 3-mL | 270 mg/vial in 500 mM Trehalose + 20 mM Histidine, pH 6.5 |
| 3 | 5-mL | 270 mg/vial in 120 mM Trehalose + 50 mM Histidine, pH 6.5 |

FIG. 7B shows the appearance of the active formulations listed above.

TABLE 23

Placebo Formulations

| Placebo Formulations | Active Formulations (~270 mg/vial) |
|---|---|
| 500 mM Trehalose + 20 mM Histidine (n = 7) | 500 mM Trehalose + 20 mM Histidine (n = 2) |
| 400 mM Trehalose + 20 mM Histidine (n = 3) | 400 mM Trehalose + 20 mM Histidine (n = 1) |
| 300 mM Trehalose + 20 mM Histidine (n = 3) | 300 mM Trehalose + 20 mM Histidine (n = 1) |

Table 24 shows the lyophilization cycle conditions for the above samples

TABLE 24

| Function | Cycle Parameters Temperature (° C.) | Hold/Rate | Rate (° C./minute) | Time (minutes) | Pressure (mTorr) |
|---|---|---|---|---|---|
| Load | 5 | Hold | — | 0 | Ambient |
| Equilibration | 5 | Hold | — | 120 | Ambient |
| Freeze | −40 | Rate | 0.25 | 180 | Ambient |
| Freeze | −40 | Hold | — | 120 | Ambient |
| Anneal | −27 | Rate | 0.25 | 52 | Ambient |
| Anneal | −27 | Hold | — | 120 | Ambient |
| Freeze | −40 | Rate | 0.25 | 52 | Ambient |
| Freeze | −40 | Hold | — | 120 | Ambient |
| Primary Drying | −30 | Rate | 0.25 | 40 | 225 |
| Primary Drying | −30 | Hold | — | 4406 | 50 |
| Secondary Drying | 25 | Rate | 0.1 | 550 | 50 |
| Secondary Drying | 25 | Hold | — | 1440 | 50 |
| Stopper | 20 | Hold | — | — | Nitrogen/Ambient |
| Unload | 20 | Hold | — | — | Ambient |

TABLE 25A

Summary of Lead Matches

| Sample Name | Color & Finish: (Sheen or Matte) | Topography: Ex. Skin, bumps, cracks, peak, curls | Structure: Dense or porous | Shrinkage | Friability | Reconstitution Time |
|---|---|---|---|---|---|---|
| SS6-3 mL Fills | | | | | | |
| Active #2 500 mM Trehalose 50 mM Histidine | off white matte | thin cracks | dense | minimal | see photo | 2 min 30 sec |

TABLE 25A-continued

Summary of Lead Matches

| Sample Name | Color & Finish: (Sheen or Matte) | Topography: Ex. Skin, bumps, cracks, peak, curls | Structure: Dense or porous | Shrinkage | Friability | Reconstitution Time |
|---|---|---|---|---|---|---|
| Placebo P2 500 mM Trehalose 20 mM Histidine | off white matte | cracks | dense | minimal | | 1 min |
| SS7-5 mL Fills | | | | | | |
| Active 500 mM Trehalose 20 mM Histidine | off white matte w/shiny specks | cracked pocked bottom | semi-dense, layered | yes, base of cake | NT | 1 min |
| Placebo 500 mM Trehalose 20 mM Histidine | off white matte w/shiny specks | cracked pocked bottom | semi-dense, more porous than active | minimal | | 20 sec unannealed: 38 sec |

Example 7: Stability of Lyophilized 270 mg TAT-NR2B9c in 20 mM Histidine Buffer pH 6.5 and 120 mM Trehalose Preparation of the Lyophilized Drug Product A small batch of TAT-NR2B9c drug product was formulated at 90 mg/mL in 20 mM Histidine pH 6.5 and 120 mM trehalose and lyophilized to evaluate solid state stability after 4 weeks at −20° C., 40° C., and 60° C. Table 25 shows the lyophilization conditions.

TABLE 25B

Lyophilization cycle conditions for Example 7

| Function | Temperature (° C.) | Hold/Rate | Rate (° C./minute) | Time (minutes) | Pressure (mTorr) |
|---|---|---|---|---|---|
| Load | 5 | Hold | — | 0 | Ambient |
| Equilibration | 5 | Hold | — | 120 | Ambient |
| Freeze | −40 | Rate | 0.5 | 90 | Ambient |
| Freeze | −40 | Hold | — | 120 | Ambient |
| Primary Drying | −28 | Rate | 0.25 | 48 | 225 |
| Primary Drying | −28 | Hold | — | 3412 | 50 |
| Secondary Drying | 25 | Rate | 0.1 | 530 | 50 |
| Secondary Drying | 25 | Hold | – | 1440 | 50 |
| Stopper | 20 | Hold | — | — | Nitrogen/Ambient |
| Unload | 20 | Hold | — | — | Ambient |

Samples were stored in constant temperature ovens with and the purity, potency, and reconstitution time in 13.2 mL (for 13.5 final volume) were assessed at 0, 1, 2 and 4 weeks. The data for each storage temperature and time is presented in Tables 26A-C.

TABLE 26A

Stability at −20° C.

| Parameter | T = 0 | | T = 4 weeks | |
|---|---|---|---|---|
| Appearance | Dense white cake | | | |
| Reconstitution Time | ~60 sec | | | |
| pH | 6.32 | | | |
| Water Content | 0.02% | | | |
| % Label Claim, TFA Method | 99.0% | | | |
| Total Purity, MSA Method (% Area) | 99.2% | | | |
| Individual Impurities | RRT | % Area | RRT | % Area |
| | 0.59 | 0.02% | 0.59 | 0.02% |
| | ND | ND | 0.95 | 0.01% |
| | 0.97 | 0.26% | 0.98 | 0.21% |
| | 1.04 | 0.26% | 1.05 | 0.32% |
| | 1.07 | 0.09% | 1.09 | 0.04% |
| | 1.10 | 0.13% | 1.11 | 0.12% |
| | ND | ND | 1.14 | 0.03% |
| | 1.15 | 0.02% | 1.16 | 0.02% |
| Deamidated NA-1, SCX Method (% Area) | <0.05% | | TBD | |

TABLE 26B

Stability at 40° C.

| Parameter | t = 0 | t = 1 week | t = 2 weeks | t = 4 weeks |
|---|---|---|---|---|
| Appearance | Dense white cake | Dense white cake | Dense white cake | Dense white cake |
| Reconstitution Time | ⁻60 sec | ⁻60 sec | ⁻60 sec | ⁻60 sec |
| pH | 6.32 | 6.55 | 6.21 | TBD |
| Water Content | 0.02% | NT | NT | NT |
| % Label Claim, TFA Method | 99.0% | 97.0% | 100.6% | 100.6% |
| Total Purity, MSA Method (% Area) | 99.2% | 99.1% | 98.9% | 99.0% |

TABLE 26B-continued

Stability at 40° C.

| Parameter | t = 0 | | t = 1 week | | t = 2 weeks | | t = 4 weeks | |
|---|---|---|---|---|---|---|---|---|
| | RRT | % Area | RRT | % Area | RRT | % Area | RRT | % Area |
| Individual Impurities | 0.59 | 0.02% | 0.59 | 0.02% | 0.62 | 0.02% | 0.59 | 0.02% |
| | 0.97 | 0.26% | 0.97 | 0.26% | 0.95 | 0.02% | 0.95 | 0.01% |
| | 1.04 | 0.26% | 1.04 | 0.25% | 0.98 | 0.21% | 0.97 | 0.17% |
| | 1.07 | 0.09% | 1.07 | 0.13% | 1.05 | 0.33% | 1.05 | 0.27% |
| | ND | ND | ND | ND | ND | ND | ND | ND |
| | 1.10 | 0.13% | 1.10 | 0.15% | 1.10 | 0.17% | 1.10 | 0.19% |
| | ND | ND | 1.13 | 0.04% | 1.13 | 0.16% | 1.13 | 0.05% |
| | 1.15 | 0.02% | 1.15 | 0.02% | 1.15 | 0.05% | 1.15 | ND |
| | ND | ND | ND | ND | 1.17 | 0.05% | 1.16 | 0.02% |
| | 1.26 | 0.01% | 1.26 | 0.01% | 1.29 | 0.01% | 1.28 | 0.01% |
| | 1.29 | 0.01% | 1.29 | 0.02% | 1.31 | 0.04% | 1.30 | 0.07% |
| Deamidated NA-1, SCX Method (% Area) | <0.05% | | NT | | NT | | TBD | |

TABLE 26C

Stability at 60° C.

| Parameter | t = 0 | | t = 1 week | | t = 2 weeks | | t = 4 weeks | |
|---|---|---|---|---|---|---|---|---|
| Appearance | Dense white cake | | Dense white cake | | Dense white cake | | Dense white cake | |
| Reconstitution Time | ~60 sec | | ~60 sec | | ~60 sec | | ~60 sec | |
| pH | 6.32 | | 6.43 | | 6.29 | | 6.29 | |
| Water Content | 0.02% | | NT | | NT | | NT | |
| % Label Claim, TFA Method | 99.0% | | 97.3% | | 101.5% | | 101.5% | |
| Total Purity, MSA Method (% Area) | 99.2% | | 98.8% | | 98.3% | | 98.0% | |
| Individual Impurities | RRT | % Area | RRT | % Area | RRT | % Area | RRT | % Area |
| | ND | ND | 0.53 | 0.01% | 0.53 | 0.01% | 0.51 | 0.02% |
| | 0.59 | 0.02% | 0.59 | 0.03% | 0.62 | 0.02% | 0.59 | 0.02% |
| | ND | ND | 0.91 | 0.01% | 0.91 | 0.02% | 0.92 | 0.01% |
| | ND | ND | 0.95 | 0.02% | 0.95 | 0.02% | 0.95 | 0.03% |
| | 0.97 | 0.26% | 0.97 | 0.26% | 0.98 | 0.25% | 0.97 | 0.20% |
| | 1.04 | 0.26% | 1.04 | 0.23% | 1.05 | 0.33 | 1.05 | 0.28% |
| | 1.07 | 0.09% | 1.07 | 0.24% | 1.07 | ND[1] | 1.08 | 0.59% |
| | 1.10 | 0.13% | 1.10 | 0.23% | 1.09 | 0.37% | 1.10 | 0.44% |
| | ND | ND | 1.12 | 0.05% | 1.12 | 0.30% | 1.13 | 0.09% |
| | 1.15 | 0.02% | 1.15 | 0.02% | 1.15 | 0.10% | 1.15 | 0.05% |
| | ND | ND | ND | ND | 1.17 | 0.07% | 1.17 | ND |
| | 1.26 | 0.01% | 1.26 | 0.01% | 1.26 | <0.01% | 1.27 | 0.01% |
| | 1.29 | 0.01% | 1.29 | 0.08% | 1.30 | 0.17% | 1.30 | 0.29% |
| Deamidated NA-1, SCX Method (% Area) | <0.05% | | NT | | NT | | TBD | |

[1] Loss in resolution around main peak

This formulation of TAT-NR2B9c is stable at −20° C. For storage temperatures of 40° C. and 60° C., potential impurities with relative retention times (RRT) of 1.07, 1.1 and 1.29 increased slowly using the MSA HPLC assay, with the largest growth appearing at 1.07 RRT. For the 40° C. storage temperature, the impurity increases from 0.09% to 0.27% over 1 month, and for the 60° C. storage temperature the impurity increases from 0.09% to 0.59%. No impurity was observed at −20° C. Impurities interpolated using the Arrhenius equation are less than 0.5% after 16 months at 25° C. or 123 months at 5° C., and less than 2% for >60 months at room temperature and many years at 5° C. Thus, this and related formulations are suitable for room temperature storage of lyophilized drug product.

This degradation study was allowed to proceed another month to confirm that the degradation products observed at 60° C. were also apparent at 40° C. These three impurities did seem to occur at the lower temperature, indicating that they are likely to be degradation products that are not specific to highly elevated temperatures. The identities of these species were determined by LC/MS/MS studies and found to all comprise acetylation of the full length TAT-NR2B9c compound. These acetylation events occurred both at the N-terminus of the peptide and on lysine side chains. Therefore, the stability of TAT-NR2B9c could be increased by either adding a scavenger or other excipients to reduce acetylation of TAT-NR2B9c in the lyophilized state or by reducing or removing the acetate so that there is a reduced chance of acetylation.

Overall Conclusions

Based on the stability, resuspension times, and lyophilization times, a preferred commercial formulation for TAT-NR2B9c is 20-100 mM Histidine, 120 mM Trehalose pH 6.5. Trehalose concentrations can be increased without a loss of stability or cake elegance but resuspension times increase with increased trehalose concentration.

Example 8: Development and Stability of a Chloride Salt of TAT-NR2B9c (TAT-NR2B9c-Cl)

Preparation of the Lyophilized Drug Product

Due to the instability of the previously developed saline formulations of TAT-NR2B9c, and the observation that acetylation of the acetate salt of TAT-NR2B9c can occur in lyophilized formulations, the acetate salt was exchanged to a chloride salt. This was done by preparative RP-HPLC using ammonium chloride. The goal of this method is to identify a novel composition of matter and a novel formulation that will allow improved stability for TAT-NR2B9c, preferably with improved stability at both room temperature and 37° C. Because TAT-NR2B9c is effective when administered to potential victims of stroke and other neurological disorders, and there is a high value to early treatment of these disorders, a formulation that is stable outside of hospital conditions would be valuable in helping the millions of people affected by these disorders every year. For example, such a drug could be stored in ambulances, or small clinics, doctor's offices or even be available to individuals, and provided to subjects having neurological disorders such as stroke or other diseases amenable to neuroprotective agents much earlier than they might be administered if they had to travel to a hospital for treatment.

General Process Protocol:
Buffer A: Water
Buffer B: Acetonitrile
Column: Daisogel ODS C-18 (1 Kg), 120 Å, 15 μm, 10 cm (Bed Volume: ~1 L)
Flow Rate: 250 mL/min.
Wavelength: 230 nm
Gradient: Kick out with 20% B (1) Column was washed with 2 Bed Volume (BV) 80% $CH_3OH$
(2) Passed 2 BV 0.025% HCl in water or 0.1% TFA in water, which was superior
(3) Loaded sample: 30 g TAT-NR2B9c acetate (PPL-NA11301) was dissolved in 1.5 L USP water (20 g/L) under which conditions, TAT-NR2B9c binds to the column;
(4) Rinsed with 200 mL USP water (also loaded to column) removing the existing acetate counterion
(5) Passed 3 BV 0.1M Ammonium Chloride ($NH_4Cl$) to supply new chloride counterion;
(6) Passed 2 BV 2%
(7) Passed 20% B (acetonitrile) to elute the product
(8) Collected fractions when the product peak eluted
(9) Fractions were analyzed by Analytical HPLC
(10) Column was back washed with 3 BV 80% $CH_3OH$ Analytical HPLC System:
YMC ODS-A C18 Column, 5 μm, 120 Å; Flow rate: 1.5 mL/min.; Wavelength: 210 nm; Temperature: 50° C.; Gradient: 20% to 35% B in 15 min.; Buffer A=0.1M $NaClO_4$ pH 3.1, Buffer B=100% ACN Synthetic Results and Discussions:

Two main pools collected from the runs were mixed and lyophilized (~5 L). 23.4 g of the final product was collected, with the purity 99.01%. The residual acetate was less than 1%. Standard refinements of the protocol should be able to increase the yield from 78% to >95%. This procedure can similarly be used to exchange a TFA salt of TAT-NR2B9c to a chloride salt, as TFA salt will bind the column in step 3 similarly.

Formulation of a Lyophilized Form of TAT-NR2B9c-Cl and Stability Testing

TAT-NR2B9c-Cl was compounded in 20 mM histidine and 120 mM trehalose, pH 6.5, for direct comparison to a previous preferred lyophilized formulation under the same lyophilization conditions at 270 mg/vial (active weight). The stability of this formulation was also compared to the previously disclosed formulation of TAT-NR2B9c-Ac resuspended in saline and lyophilized. For the latter, a small batch of TAT-NR2B9c-acetate drug product was formulated at 90 mg/mL in saline (no other excipients) and lyophilized at 270 mg/vial. Stability of the formulations in the lyophilized state was evaluated after 4 weeks at −20° C. (control), 40° C. and 60° C.

TABLE 27

Stability of TAT-NR2B9c-Cl (20 mM histidine, 120 mM trehalose) versus TAT-NR2B9c-Ac (saline)

| | NA-1-Chloride salt stability data | | | | | NA-1-Ac SALINE stability data | | | |
|---|---|---|---|---|---|---|---|---|---|
| RP-HPLC TFA | 0.899 | | | 0.11 | RP-HPLC TFA | 0.899 | | | |
| | 0.95 | | | | | 0.95 | | | 0.11 |
| | 0.97 | | | 0.07 | | 0.97 | | | 0.09 |
| | 0.98 | | | | | 0.98 | | | 0.08 |
| | 0.99 | 0.17 | 0.29 | 0.43 | | 0.99 | 0.18 | 0.23 | 0.19 |
| | 1 | 98 | 97.78 | 96.64 | | 1 | 97.93 | 97.42 | 94.84 |
| | 1.02 | 1.27 | 1.22 | 1.36 | | 1.02 | 1.22 | 1.39 | 2.07 |
| | 1.03 | 0.11 | 0.11 | 0.16 | | 1.03 | 0.1 | 0.1 | 0.12 |
| | 1.05 | 0.08 | 0.07 | 0.09 | | 1.05 | 0.05 | 0.16 | 0.61 |
| | 1.06 | | | | | 1.06 | | | |
| | 1.07 | 0.22 | 0.24 | 0.46 | | 1.07 | 0.2 | 0.19 | 0.28 |
| | 1.08 | | | | | 1.08 | | | 0.1 |
| | 1.09 | | | 0.06 | | 1.09 | | | 0.07 |
| | 1.1 | | 0.11 | 0.09 | | 1.1 | | | 0.12 |
| | 1.11 | 0.16 | | 0.09 | | 1.11 | 0.05 | 0.06 | 0.14 |
| | 1.12 | | 0.11 | | | 1.12 | 0.17 | 0.17 | 0.31 |
| | 1.13 | | 0.06 | | | 1.13 | 0.05 | 0.28 | 0.72 |
| | 1.14 | | | 0.09 | | 1.14 | 0.06 | | |
| | 1.18 | | | | | 1.18 | | | |
| | 1.19 | | | | | 1.19 | | | |
| | 1.26 | | | | | 1.26 | | | |
| | 1.34 | | | | | 1.34 | | | |
| | 1.36 | | | | | 1.36 | | | |
| | 1.4 | | | | | 1.4 | | | |
| | 1.48 | | | | | 1.48 | | | |

TABLE 27-continued

Stability of TAT-NR2B9c-Cl (20 mM histidine, 120 mM trehalose) versus TAT-NR2B9c-Ac (saline)

| | NA-1-Chloride salt stability data | | | | | NA-1-Ac SALINE stability data | | | |
|---|---|---|---|---|---|---|---|---|---|
| RP-HPLC-MSA | 0.94 | | | 0.07 | RP-HPLC-MSA | 0.94 | | | 0.05 |
| | 0.98 | 0.11 | 0.11 | 0.15 | | 0.98 | 0.06 | 0.07 | 0.08 |
| | 1 | 99.3 | 99.14 | 98.68 | | 1 | 99.13 | 98.89 | 96.38 |
| | 1.02 | | | | | 1.02 | | | |
| | 1.03 | 0.27 | 0.31 | 0.3 | | 1.03 | 0.41 | 0.32 | 0.42 |
| | 1.04 | 0.07 | 0.06 | 0.09 | | 1.04 | 0.09 | 0.09 | |
| | 1.06 | 0.25 | 0.26 | 0.55 | | 1.06 | 0.23 | 0.21 | 0.22 |
| | 1.07 | | 0.12 | 0.09 | | 1.07 | 0.08 | 0.21 | 1.17 |
| | 1.08 | | | | | 1.08 | | | |
| | 1.1 | | | 0.07 | | 1.1 | | 0.01 | 0.59 |
| | 1.12 | | | | | 1.12 | | | 0.07 |
| | 1.14 | | | | | 1.14 | | | 0.1 |
| | 1.16 | | | | | 1.16 | | | 0.06 |
| | 1.2 | | | | | 1.2 | | 0.06 | 0.31 |
| | 1.23 | | | | | 1.23 | | | |
| | 1.24 | | | | | 1.24 | | | |
| | 1.27 | | | | | 1.27 | | | |
| | 1.3 | | | | | 1.3 | | 0.06 | 0.54 |

TABLE 28

Stability of TAT-NR2B9c-Cl (20 mM histidine, 120 mM trehalose) versus TAT-NR2B9c-Ac (saline) at 11 months

| Peak | | NA-1-Chloride salt T = 11 months | | | NA-1-Ac in saline T = 11 months | | |
|---|---|---|---|---|---|---|---|
| | (RRT) | −20 C. | 40 C. | 60 C. | −20 C. | 40 C. | 60 C. |
| RP-HPLC-TFA | 0.899 | | | 0.1 | | | |
| | 0.93 | | | 0.18 | | | |
| | 0.95 | | | 0.16 | | | 0.27 |
| | 0.97 | | | 0.1 | | | 0.17 |
| | 0.99 | | 0.29 | 0.38 | | | 0.22 |
| | 1 | 98.57 | 98.14 | 95.49 | 98.57 | 96.48 | 81.27 |
| | 1.02 | 1.18 | 1.09 | 1.42 | 1.14 | 1.8 | 6.51 |
| | 1.03 | 0.07 | 0.09 | 0.34 | 0.09 | | |
| | 1.05 | | 0.05 | 0.17 | | 0.51 | 3 |
| | 1.06 | | | 0.15 | | 0.06 | 0.27 |
| | 1.07 | 0.18 | 0.36 | 1.05 | 0.2 | 0.27 | 0.62 |
| | 1.08 | | | | | 0.08 | 0.3 |
| | 1.09 | | | | | | 0.16 |
| | 1.1 | | | | | 0.06 | 0.28 |
| | 1.11 | | | | | | 0.29 |
| | 1.12 | | | 0.12 | | | 0.33 |
| | 1.13 | | | | | 0.41 | 3.49 |
| | 1.15 | | | | | | 0.42 |
| | 1.16 | | | | | | 0.16 |
| | 1.17 | | | | | | 0.26 |
| | 1.18 | | | | | | 0.1 |
| | 1.19 | | | | | | 0.23 |
| | 1.2 | | | | | | 0.26 |
| | 1.22 | | | | | | 0.19 |
| | 1.23 | | | | | | 0.3 |
| | 1.24 | | | | | | 0.25 |
| | 1.26 | | | | | | 0.34 |
| | 1.261 | | | | | | 0.34 |
| | 1.34 | | | | | | 0.14 |
| | | NA-1-Chloride salt | | | NA-1-Ac in saline | | |
| RP-HPLC-MSA | 0.52 | | | | | | 0.13 |
| | 0.87 | | | 0.13 | | | |
| | 0.91 | | 0.05 | 0.2 | | | 0.23 |
| | 0.94 | | 0.09 | 0.34 | | | 0.29 |
| | 0.98 | 0.1 | 0.12 | 0.21 | 0.1 | 0.12 | 0.1 |
| | 1 | 99.3 | 98.71 | 95.34 | 99.32 | 97.08 | 87.12 |
| | 1.02 | 0.29 | 0.24 | 0.61 | 0.24 | 0.28 | 0.82 |
| | 1.04 | 0.07 | 0.12 | | | 0.08 | 0.11 |
| | 1.06 | 0.25 | 0.48 | 1.48 | | | |
| | 1.07 | 0.06 | 0.25 | 0.25 | | 1.03 | 6.36 |
| | 1.09 | | 0.08 | 0.26 | | 0.45 | 3.02 |
| | 1.1 | | | | | | |
| | 0.27 | | | | | | |
| | 1.12 | | | | | 0.05 | 0.23 |
| | 1.14 | | 0.17 | | | | 0.31 |
| | 1.15 | | | | | | 0.53 |
| | 1.16 | | 0.11 | | | 0.26 | |
| | 1.19 | | | | | | 0.33 |
| | 1.2 | | | | | | 0.1 |
| | 1.23 | 0.05 | 0.24 | | | 0.1 | 0.59 |
| | 1.24 | | | | | 0.06 | 0.59 |
| | 1.25 | | 0.18 | | | | 0.35 |
| | 1.26 | | | | | 0.05 | 0.44 |
| | 1.27 | | | | | 0.41 | 3.18 |
| | 1.33 | | | | | | 0.26 |
| | 1.35 | | | | | | 0.15 | pTable 27 shows the relative area of each peak observed in each HPLC assay at each temperature after 1 month of storage and at each relative retention time (peak identity) for direct comparison. For both formulations and methods, the starting purities are very similar (98% for TAT-NR2B9c-Cl vs 97.93% for TAT-NR2B9c-Ac by the TFA method, and 99.3% vs 99.13% for the methanesulfonic acid (MSA) method. Looking at the 60° C. data, the TAT-NR2B9c-Cl histidine trehalose composition is substantially more stable than the TAT-NR2B9c saline formulation by both methods. For the TFA method after 1 month of storage at 60° C., the TAT-NR2B9c-Cl salt retains 98.6% of the main peak whereas the TAT-NR2B9c-Ac saline formulation only retains 96.8% of the starting material. For the MSA method, the difference is even more striking, where the TAT-NR2B9c-Cl salt retains 99.4% of its starting material whereas the TAT-NR2B9c-Ac saline formation only retains 97.2% of its starting material.

Table 28 shows the relative area of each peak observed in each HPLC assay at in the same samples after 11 months at the different storage temperatures. These data support the improved stability of the NA-1 Cl salt formulation versus the NA-1-Ac formulation in chloride. Comparing the area of the main NA-1 peaks in the TFA assay at 40° C., which is the accelerated condition by ICH guidance to support room temperature storage of a lyophilized drug, the NA-1-Cl retains 98.14% purity from a starting purity of 98.58, while the NA-1-Ac in saline has dropped from 98.57 pure to 96.48, which is below the purity specification of 97% and would not be considered stable after about a year. The same trend is observed for the MSA assay from 99.3% pure to 98.71 pure for NA-1-Cl and 97.08 for NA-1-Ac in saline. Examining the 60° C. purity results after 11 months (Table 28), the differences are significantly more profound, with NA-1-Cl being significantly more stable than NA-1-Ac From a clinical standpoint, example purity limits for a drug for humans may be 97% purity with no uncharacterized impurity over 0.5% at the rated storage condition. Using the Arrhenius equation, we can use the 40° C. and 60° C. stability data to predict the drop in purity of the main peak or the growth of the observed impurities at different storage temperatures (e.g., 25° C. or 37° C. versus the observed 40° C. or 60° C. data). Assuming that the drug would be stored at ambient temperature, it would be useful to demonstrate stability at 37° C. because there would be many environments without refrigeration where the ambient temperature in the summer could be in this range. Assuming a purity requirement of 97.0% at 37° C., and using the representative stability data from the TFA assay for main peak purity because it is the most sensitive (i.e., shows the biggest decline in purity at 40° C. and 60° C.), the saline formulation would be predicted to have a shelf life of 29.8 months (or a little over 2 years), whereas the TAT-NR2B9c-C1 formulation would have a shelf life of ~500 months, or approximately 41 years. This is a significant improvement in stability.

From the standpoint of the growth of the largest impurity (aside from the impurity at relative retention time (RTT) 1.02 by the TFA method which is an identified impurity), the largest impurity growth after 1 month for the TAT-NR2B9c-Cl formulation is 0.17 to 0.43 (RRT 0.99 by the TFA method), whereas the largest impurity growth for the TAT-NR2B9c-Ac saline formulation is 0.05-0.72 (1.13 RRT by the TFA method). Assuming the impurity limit above as 0.5% at 37° C., and using the Arrhenius equation along with the 40C and 60C data from each of these impurities, the saline formulation is predicted to have a shelf life of ~4.8 months at 37° C. whereas the shelf life of the TAT-NR2B9c-C1 composition is predicted to be >10 years. Thus, from either the standpoint of the total level of TAT-NR2B9c or the growth of the largest impurity, the TAT-NR2B9c-C1 composition is a significant improvement over the saline formulation.

Example 9: TAT-NR2B9c-Cl is More Stable than TAT-NR2B9c-Ac in Histidine, Trehalose Formulations TAT-NR2B9c-Cl and TAT-NR2B9c-Ac were both formulated at 90 mg/mL in 20 mM Histidine, 120 mM trehalose pH 6.5. Three milliliter aliquots (270 mg) of each were lyophilized under the same program as presented supra, and on completion were placed into constant temperature and humidity incubators at −20° C. (control), 40° C. and 60° C. After 4 weeks, the stability of each formulation was tested using two orthogonal HPLC methods—one with TFA as the carrier and one with MSA as the carrier.

Table 29 shows the relative area of each peak observed in each of the two HPLC assays at each temperature after 1 month of storage and at each relative retention time (RRT; peak identity) for direct comparison. The left panel represents the TAT-NR2B9c-Ac formulation and the right panel shows the results of the TAT-NR2B9c-Cl salt formulation. The peak at an RRT of 1 corresponds to the intact TAT-NR2B9c peptide in each assay and column. For both formulations and methods, the starting purities are very similar (98% for TAT-NR2B9c-Cl vs 98.3% for TAT-NR2B9c-Ac by the TFA method, and 99.3% vs 99.2% respectively for the MSA method). Looking at the 60° C. data, the TAT-NR2B9c-Cl composition is substantially more stable than the TAT-NR2B9c-Ac formulation by both methods. For the TFA method after 1 month of storage at 60° C., the TAT-NR2B9c-Cl salt retains 98.6% of the main peak (96.64% divided by 98% starting) whereas the TAT-NR2B9c-Ac saline formulation only retains 96% of the starting material (94.44% divided by 98.3% starting purity). Form the MSA method, the difference is even more striking, where the TAT-NR2B9c-Cl salt retains 99.4% of its starting material (98.68%/99.3%) whereas the TAT-NR2B9c-Ac saline formation only retains 95.6% of its starting material (94.81%/99.2%). When one looks at the largest impurities for either composition, it is clear that for both the 40° C. and 60° C. accelerated stability conditions that the TAT-NR2B9c-acetate salt has larger impurities and is thus less stable. The chloride salt of TAT-NR2B9c is surprisingly more stable than the acetate salt under identical conditions.

Table 30 shows the relative area of each peak observed in each HPLC assay at in the same samples after 11 months at the different storage temperatures. These data support the improved stability of the NA-1 Cl salt formulation versus the NA-1-Ac salt when formulated in the exact same buffer (20 mM Histidine/120 mM Trehalose pH 6.5). Comparing the area of the main NA-1 peaks in the TFA assay at 40° C., which is the accelerated condition by ICH guidance to support room temperature storage of a lyophilized drug, the NA-1-0 retains 98.14% purity from a starting purity of 98.58, while the NA-1-Ac in saline has dropped from 98.57 pure to 95.91, which is below the purity specification of 97% and would not be considered stable. The same trend is observed for the MSA assay from 99.3% pure to 98.71 pure for NA-1-0 and 96.85% for NA-1-Ac in saline. Examining the 60° C. purity results after 11 months (Table 30), the differences are significantly more profound, with NA-1-0 being significantly more stable than NA-1-Ac (~95% pure for both assays for the chloride salt vs ~83% pure for the acetate salt). Thus, the NA-1 chloride salt is predicted to be surprisingly and significantly more stable than the acetate salt in the same buffer.

TABLE 29

Stability of TAT-NR2B9c-Ac versus TAT-NR2B9c-Cl lyophilized in 20 mM Histidine 120 mM Trehalose pH 6.5 at 4 weeks

| | | T = 4 weeks | | | | | T = 4 weeks | | |
| --- | --- | --- | --- | --- | --- | --- | --- | --- | --- |
| | RRT | −20 C. | 40 C. | 60 C. | | RRT | −20 C. | 40 C. | 60 C. |
| RP- | 0.86 | | | | RP- | 0.86 | | | |
| HPLC | 0.88 | | | | HPLC | 0.88 | | | |
| TFA | 0.9 | | | | TFA | 0.9 | | | 0.11 |

TABLE 29-continued

Stability of TAT-NR2B9c-Ac versus TAT-NR2B9c-Cl lyophilized
in 20 mM Histidine 120 mM Trehalose pH 6.5 at 4 weeks

|  |  |  |  |  |  |  |
|---|---|---|---|---|---|---|
| 0.93 | | | 0.93 | | | |
| 0.95 | | | 0.95 | | | |
| 0.97 | 0.06 | | 0.97 | | | 0.07 |
| 0.98 | | | 0.98 | | | |
| 0.99 | 0.58 | 0.56 | 0.99 | 0.17 | 0.29 | 0.43 |
| 1 | 97.19 | 94.44 | 1 | 98 | 97.78 | 96.64 |
| 1.02 | 1.52 | 2.18 | 1.02 | 1.27 | 1.22 | 1.36 |
| 1.03 | 0.12 | 0.13 | 1.03 | 0.11 | 0.11 | 0.16 |
| 1.04 | 0.15 | 0.71 | 1.04 | | | |
| 1.05 | | | 1.05 | 0.08 | 0.07 | 0.09 |
| 1.06 | 0.07 | 0.17 | 1.06 | | | |
| 1.07 | 0.23 | 0.36 | 1.07 | 0.22 | 0.24 | 0.46 |
| 1.08 | | 0.16 | 1.08 | | | |
| 1.09 | | 0.15 | 1.09 | | | 0.06 |
| 1.1 | | 0.18 | 1.1 | | 0.11 | 0.09 |
| 1.11 | | 0.21 | 1.11 | 0.16 | | 0.09 |
| 1.12 | | | 1.12 | | 0.11 | |
| 1.13 | 0.09 | 0.75 | 1.13 | | 0.06 | |
| 1.14 | | | 1.14 | | | 0.09 |
| 1.26 | | | 1.26 | | | |
| 1.34 | | | 1.34 | | | |
| 1.4 | | | 1.4 | | | |
| 1.48 | | | 1.48 | | | |

|  | −20 C. | 40 C. | 60 C. |  | −20 C. | 40 C. | 60 C. |
|---|---|---|---|---|---|---|---|
| RP- | 0.77 | | | RP- | 0.77 | | |
| HPLC- | 0.94 | | 0.09 | HPLC- | 0.94 | | 0.07 |
| MSA | 0.98 | 0.12 | 0.19 | MSA | 0.98 | 0.11 | 0.11 | 0.15 |
| | 0.99 | 0.7 | 0.6 | | 0.99 | | | |
| | 1 | 98.11 | 94.81 | | 1 | 99.3 | 99.14 | 98.68 |
| | 1.02 | 0.34 | 0.38 | | 1.02 | | | |
| | 1.03 | 0.1 | 0.17 | | 1.03 | 0.27 | 0.31 | 0.3 |
| | 1.04 | | | | 1.04 | 0.07 | 0.06 | 0.09 |
| | 1.06 | 0.4 | 1.46 | | 1.06 | 0.25 | 0.26 | 0.55 |
| | 1.07 | | | | 1.07 | | 0.12 | 0.09 |
| | 1.08 | 0.14 | 0.64 | | 1.08 | | | |
| | 1.1 | | 0.17 | | 1.1 | | | 0.07 |
| | 1.12 | | 0.14 | | 1.12 | | | |
| | 1.13 | | 0.06 | | 1.13 | | | |
| | 1.14 | | | | 1.14 | | | |
| | 1.15 | | 0.19 | | 1.15 | | | |
| | 1.16 | | | | 1.16 | | | |
| | 1.17 | | 0.09 | | 1.17 | | | |
| | 1.18 | | 0.07 | | 1.18 | | | |
| | 1.2 | | | | 1.2 | | | |
| | 1.23 | | 0.17 | | 1.23 | | | |
| | 1.24 | | 0.18 | | 1.24 | | | |
| | 1.27 | 0.08 | 0.59 | | 1.27 | | | |
| | 1.3 | | | | 1.3 | | | |

TABLE 30

Stability of TAT-NR2B9c-Ac versus TAT-NR2B9c-Cl lyophilized
in 20 mM Histidine 120 mM Trehalose pH 6.5 after 11 months

| | Peak | NA-1 250 MM His, 120 mM Trehalose pH 6.5 T = 11 months | | | NA-1 Chloride salt stability data T-11 months | | |
|---|---|---|---|---|---|---|---|
| | (RRT) | −20 C. | 40 C. | 60 C. | −20 C. | 40 C. | 60 C. |
| RP- | 0.86 | | 0.12 | 0.52 | | | |
| HPLC | 0.88 | | | 0.17 | | | |
| TFA | 0.899 | | | 0.15 | | | 0.1 |
| | 0.93 | | | | | | 0.18 |
| | 0.95 | | | 0.14 | | | 0.16 |
| | 0.97 | | | 0.19 | | | 0.1 |
| | 0.99 | | 0.37 | 0.63 | | 0.29 | 0.38 |
| | 1 | 98.47 | 95.91 | 83.08 | 98.57 | 98.14 | 95.49 |
| | 1.02 | 1.21 | 1.93 | 5.77 | 1.18 | 1.09 | 1.42 |
| | 1.03 | 0.08 | | | 0.07 | 0.09 | 0.34 |
| | 1.05 | 0.05 | 0.57 | 3.45 | 0.05 | | 0.17 |
| | 1.07 | | 0.07 | 0.19 | | | 0.15 |

TABLE 30-continued

Stability of TAT-NR2B9c-Ac versus TAT-NR2B9c-Cl lyophilized
in 20 mM Histidine 120 mM Trehalose pH 6.5 after 11 months

|  |  |  |  |  |  |  |
|---|---|---|---|---|---|---|
| 1.07 | 0.19 | 0.31 | 0.75 | 0.18 | 0.36 | 1.05 |
| 1.08 |  | 0.11 | 0.39 |  |  |  |
| 1.09 |  | 0.07 | 0.27 |  |  |  |
| 1.1  |  | 0.07 | 0.31 |  |  |  |
| 1.12 |  | 0.06 | 0.29 |  |  | 0.12 |
| 1.13 |  | 0.41 | 2.5  |  |  |  |
| 1.15 |  |      | 0.19 |  |  |  |
| 1.17 |  |      | 0.2  |  |  |  |
| 1.2  |  |      | 0.11 |  |  |  |
| 1.22 |  |      | 0.12 |  |  |  |
| 1.23 |  |      | 0.12 |  |  |  |
| 1.25 |  |      | 0.12 |  |  |  |

|  | NA-1 250 mM His, 120 mM Trehalose pH 6.5 | | | NA-1 Chloride salt | | |
|---|---|---|---|---|---|---|
| RP-HPLC-MSA | 0.77 |  | 0.08 | 0.48 |  |  |
|  | 0.8  |  |      | 0.14 |  |  |
|  | 0.87 |  |      |      |  | 0.13 |
|  | 0.91 |  |      | 0.15 | 0.05 | 0.2 |
|  | 0.94 |  | 0.05 | 0.14 | 0.09 | 0.34 |
|  | 0.945|  |      | 0.22 |  |  |
|  | 0.98 | 0.11 | 0.23 | 0.85 | 0.1 | 0.12 | 0.21 |
|  | 1    | 99.23 | 96.85 | 82.73 | 99.3 | 98.71 | 95.34 |
|  | 1.02 | 0.32 | 0.35 | 0.77 | 0.29 | 0.24 | 0.61 |
|  | 1.04 | 0.08 | 0.11 | 0.77 | 0.07 | 0.12 |  |
|  | 1.06 | 0.26 | 1.07 | 5.05 | 0.25 | 0.48 | 1.48 |
|  | 1.07 |  |  |  |  | 0.06 | 0.25 |
|  | 1.09 |  | 0.56 | 3.42 |  | 0.08 | 0.26 |
|  | 1.1  |  | 0.08 | 0.41 |  |  |  |
|  | 1.12 |  | 0.07 | 0.32 |  |  |  |
|  | 1.14 |  |      | 0.28 |  |  | 0.17 |
|  | 1.15 |  | 0.09 | 0.32 |  |  |  |
|  | 1.16 |  |      |      |  |  | 0.11 |
|  | 1.19 |  |      | 0.27 |  |  |  |
|  | 1.23 |  | 0.07 | 0.37 |  | 0.05 | 0.24 |
|  | 1.24 |  |      | 0.22 |  |  |  |
|  | 1.25 |  |      |      |  |  | 0.18 |
|  | 1.26 |  |      | 0.19 |  |  |  |
|  | 1.27 |  | 0.38 | 2.47 |  |  |  |
|  | 1.35 |  |      | 0.12 |  |  |  |

What is claimed is:

1. A method of preparing a formulation comprising synthesizing a chloride salt of a peptide, which is TAT-NR2B9c (SEQ ID NO:6) or differs from TAT-NR2B9c by up to 5 amino acid substitutions, insertions or deletions, wherein greater than 95% by moles of all anions in the salt are chloride, and incorporating the chloride salt into a formulation.

2. The method of claim 1, wherein the peptide is TAT-NR2B9c.

3. The method of claim 1, wherein the synthesizing comprises exchanging trifluoroacetate for chloride in a trifluoroacetate salt of TAT-NR2B9c.

4. The method of claim 1, wherein the synthesizing comprises exchanging trifluoroacetate for acetate and then acetate for chloride starting from a trifluoroacetate salt of TAT-NR2B9c.

5. The method of claim 1, wherein greater than 99% by moles of all anions in the salt are chloride.

6. The method of claim 1, wherein the formulation further comprises a buffer and a sugar.

7. The method of claim 6, wherein the buffer is histidine and the sugar is trehalose and the pH is 6-7.

8. The method of claim 6, wherein acetate and trifluoroacetate each comprise less than 1% of anions by weight in the formulation.

9. The method of claim 6, wherein acetate and trifluoroacetate each comprise less than 0.1% by weight of anions in the formulation.

10. The method of claim 7, wherein the chloride salt of the peptide is at a concentration of 70-120 mg/ml, the histidine is at a concentration of 15-100 mM, and the trehalose is at a concentration of 80-160 mM.

11. The method of claim 10, wherein the chloride salt of the peptide is at a concentration of 70-120 mg/ml, the histidine is at a concentration of 20-100 mM, and the trehalose is at a concentration of 100-140 mM.

12. The method of claim 7, wherein the chloride salt of the peptide is at a concentration of 70-120 mg/ml and the peptide is TAT-NR2B9c, the histidine is at a concentration of 20-50 mM, and the trehalose is at a concentration of 100-140 mM.

13. The method of claim 7, wherein the histidine is at a concentration of 20 mM and the trehalose is at a concentration of 120 mM and the chloride salt of the peptide is at a concentration of 90 mg/ml and the peptide is TAT-NR2B9c.

14. The method of claim 1, wherein the formulation is lyophilized.

15. The method of claim 1, wherein acetate and trifluoroacetate each comprise less than 1% by weight of anions in the formulation.

16. The method of claim 15, wherein acetate and trifluoroacetate each comprise less than 0.1% by weight of anions in the formulation.

17. The method of claim 14, further comprising reconstituting the lyophilized formulation with an aqueous solution.

18. The method of claim 17, wherein the reconstituted formulation comprises histidine at a concentration of 4-20 mM and trehalose at a concentration of 20-30 mM and the pH is 6-7.

19. The method claim 17, wherein acetate and trifluoroacetate each comprise less than 1% by weight of anions in the reconstituted formulation.

20. The method of claim 17, wherein acetate and trifluoroacetate each comprise less than 0.1% by weight of anions in the reconstituted formulation.

21. The method of claim 14, further comprising storing the lyophilized formulation for at least a week at a temperature of at least 20° C.; and
reconstituting the lyophilized formulation.

22. The method of claim 21, wherein the lyophilized formulation is reconstituted in water or saline.

23. The method of claim 21, further comprising administering the reconstituted formulation, optionally after further dilution in normal saline, to a patient.

24. The method of claim 23, wherein the formulation is stored for at least a year.

25. The method of claim 24, wherein the storage is at ambient temperature.

26. The method of claim 24, wherein the storage includes periods in which the temperature exceeds 37° C.

27. The method of claim 23, wherein the patient has stroke or traumatic injury to the CNS.

28. The method of claim 1, wherein the formulation comprises a phosphate buffer.

29. The method of claim 28, wherein the phosphate buffer is sodium phosphate at 50 mM and the formulation further comprises sodium chloride at 76.9 mM and is at pH 7.0.

30. The method of claim 1, wherein acetate and trifluoroacetate each comprise less than 5% of anions by moles in the formulation.

* * * * *

UNITED STATES PATENT AND TRADEMARK OFFICE
CERTIFICATE OF CORRECTION

| | |
|---|---|
| PATENT NO. | : 11,266,714 B2 |
| APPLICATION NO. | : 16/904230 |
| DATED | : March 8, 2022 |
| INVENTOR(S) | : Jonathan David Garman |

It is certified that error appears in the above-identified patent and that said Letters Patent is hereby corrected as shown below:

In the Claims

In Column 76, Line 1, Claim 19, delete "The method claim" and insert -- The method of claim --, therefor.

Signed and Sealed this
First Day of August, 2023

Katherine Kelly Vidal
*Director of the United States Patent and Trademark Office*